US012642699B2

(12) United States Patent
Holland et al.

(10) Patent No.: US 12,642,699 B2
(45) Date of Patent: Jun. 2, 2026

(54) SYSTEM AND METHOD FOR LASER TREATMENT OF OCULAR TISSUE USING NON-COLLINEAR IMAGING

(71) Applicant: ViaLase, Inc., Aliso Viejo, CA (US)

(72) Inventors: Guy Holland, San Juan Capistrano, CA (US); Reza Khazaeinezhad, Lake Forest, CA (US); Wesley W. Lummis, Rancho Santa Margarita, CA (US); Ferenc Raksi, Mission Viejo, CA (US); Manu Sharma, Ladera Ranch, CA (US)

(73) Assignee: ViaLase, Inc., ALiso Viejo, CA (US)

( * ) Notice: Subject to any disclaimer, the term of this patent is extended or adjusted under 35 U.S.C. 154(b) by 759 days.

(21) Appl. No.: 17/889,864

(22) Filed: Aug. 17, 2022

(65) Prior Publication Data

US 2024/0058172 A1 Feb. 22, 2024

(51) Int. Cl.
A61F 9/008 (2006.01)

(52) U.S. Cl.
CPC ..................... *A61F 9/00825* (2013.01); *A61F 2009/00851* (2013.01); *A61F 2009/00861* (2013.01)

(58) Field of Classification Search
CPC ........ A61F 9/00825; A61F 2009/00851; A61F 2009/00861
See application file for complete search history.

(56) References Cited

U.S. PATENT DOCUMENTS

| | | | |
|---|---|---|---|
| 4,423,931 | A | 1/1984 | Shapiro |
| 5,123,902 | A | 6/1992 | Müller et al. |

(Continued)

FOREIGN PATENT DOCUMENTS

| | | |
|---|---|---|
| CN | 104382689 B | 9/2016 |
| CN | 113662507 A | 11/2021 |

(Continued)

OTHER PUBLICATIONS

Grant, "Tonographic method for measuring the facility and rate of aqueous flow in human eyes". Arch. Ophthalmol. 44(2), pp. 204-214 (1950).

(Continued)

*Primary Examiner* — Niketa Patel
*Assistant Examiner* — Skylar Lindsey Christianson
(74) *Attorney, Agent, or Firm* — LOZA & LOZA, LLP; David S. Sarisky

(57) ABSTRACT
A method of treating an eye includes delivering an OCT beam along an OCT optical path that enters a first optical subsystem along an input axis, and exits the first optical subsystem along an output axis that: 1) is substantially parallel to the optical axis of the eye, 2) is radially offset from the optical axis, and 3) extends through the cornea and into a portion of the irido-corneal angle at a point along a circumferential angle of the eye. The method also includes imaging the portion of the irido-corneal angle with the OCT beam; delivering a laser beam along an angled optical path that extends through the first optical subsystem, through the cornea, through the anterior chamber, and into a target volume of ocular tissue in the portion of the irido-corneal angle; and photodisrupting at least a portion of the target volume of ocular tissue with the laser beam.

13 Claims, 27 Drawing Sheets

(56) References Cited

U.S. PATENT DOCUMENTS

| | | | |
|---|---|---|---|
| 5,549,596 A | 8/1996 | Latina | |
| 6,004,314 A | 12/1999 | Wei et al. | |
| 6,033,396 A | 3/2000 | Huang et al. | |
| 6,059,772 A | 5/2000 | Hsia et al. | |
| 6,251,103 B1 | 6/2001 | Berlin | |
| 6,482,199 B1 | 11/2002 | Neev | |
| 6,525,875 B1 | 2/2003 | Lauer | |
| 6,682,523 B2 | 1/2004 | Shadduck | |
| 6,989,007 B2 | 1/2006 | Shadduck | |
| 7,131,968 B2 | 11/2006 | Bendett et al. | |
| 7,192,412 B1 | 3/2007 | Zhou et al. | |
| 7,282,046 B2 | 10/2007 | Simon | |
| 7,351,241 B2 | 4/2008 | Bendett et al. | |
| 7,771,417 B2 | 8/2010 | Telfair et al. | |
| 8,011,504 B1 | 9/2011 | Farberov | |
| 8,171,937 B2 | 5/2012 | Bendett et al. | |
| 8,230,866 B2 | 7/2012 | Hauger et al. | |
| 8,394,084 B2 | 3/2013 | Palankar et al. | |
| 8,523,926 B2 | 9/2013 | Neev | |
| 8,540,659 B2 | 9/2013 | Berlin | |
| 8,568,393 B2 | 10/2013 | Palanker | |
| 8,585,686 B2 | 11/2013 | Bergt et al. | |
| 8,679,089 B2 | 3/2014 | Berlin | |
| 8,687,866 B2 | 4/2014 | Marziliano et al. | |
| 8,709,001 B2 | 4/2014 | Blumenkranz et al. | |
| 8,747,395 B2 | 6/2014 | Rathjen | |
| 8,845,624 B2 | 9/2014 | Raksi et al. | |
| 8,920,407 B2 | 12/2014 | Raksi et al. | |
| 9,028,069 B2 | 5/2015 | Rathjen | |
| 9,033,963 B2 | 5/2015 | Vera et al. | |
| 9,044,303 B2 | 6/2015 | Kurtz et al. | |
| 9,101,448 B2 | 8/2015 | Blumenkranz et al. | |
| 9,259,153 B2 | 2/2016 | Goto | |
| 9,259,354 B2 | 2/2016 | Horvath et al. | |
| 9,265,411 B2 | 2/2016 | Chen et al. | |
| 9,271,870 B2 | 3/2016 | Palanker et al. | |
| 9,301,878 B2 | 4/2016 | Raksi et al. | |
| 9,320,650 B2 | 4/2016 | Bendett et al. | |
| 9,441,946 B2 | 9/2016 | Massow et al. | |
| 9,456,925 B2 | 10/2016 | Kurtz et al. | |
| 9,474,648 B2 | 10/2016 | Palanker et al. | |
| 9,498,295 B2 | 11/2016 | Palanker | |
| 9,517,006 B2 | 12/2016 | Izatt et al. | |
| 9,554,702 B2 | 1/2017 | Papac et al. | |
| 9,560,963 B2 | 2/2017 | Buckland et al. | |
| 9,603,741 B2 | 3/2017 | Berlin | |
| 9,603,744 B2 | 3/2017 | Hailmann et al. | |
| 9,629,750 B2 | 4/2017 | Dambacher et al. | |
| 9,642,746 B2 | 5/2017 | Berlin | |
| 9,681,985 B2 | 6/2017 | Andersen et al. | |
| 9,724,238 B2 | 8/2017 | Heitel | |
| 9,750,640 B2 | 9/2017 | Palanker et al. | |
| 9,820,883 B2 | 11/2017 | Berlin | |
| 9,833,357 B2 | 12/2017 | Berlin | |
| 9,844,464 B2 | 12/2017 | Bendett et al. | |
| 9,936,868 B2 | 4/2018 | Izatt et al. | |
| 10,064,757 B2 | 9/2018 | Berlin | |
| 10,073,515 B2 | 9/2018 | Awdeh | |
| 10,159,600 B2 | 12/2018 | Horvath et al. | |
| 10,159,601 B2 | 12/2018 | Berlin | |
| 10,165,941 B2 | 1/2019 | Walsh et al. | |
| 10,179,066 B2 | 1/2019 | Badawi et al. | |
| 10,195,078 B2 | 2/2019 | Horvath et al. | |
| 10,195,079 B2 | 2/2019 | Horvath et al. | |
| 10,195,080 B2 | 2/2019 | Berlin | |
| 10,238,281 B2 | 3/2019 | Isogai et al. | |
| 10,238,541 B2 | 3/2019 | Yee et al. | |
| 10,292,868 B2 | 5/2019 | Chew et al. | |
| 10,335,314 B2 | 7/2019 | Berlin | |
| 10,335,315 B2 | 7/2019 | Goldshleger et al. | |
| 10,360,683 B2 | 7/2019 | Iwase et al. | |
| 10,362,935 B2 | 7/2019 | Pastmalchi et al. | |
| 10,362,936 B2 | 7/2019 | Buckland et al. | |
| 10,363,169 B2 | 7/2019 | Belkin et al. | |
| 10,363,172 B2 | 7/2019 | Kawai et al. | |
| 10,383,689 B2 | 8/2019 | Berlin | |
| 10,390,883 B2 | 8/2019 | Deladurantaye et al. | |
| 10,398,306 B2 | 9/2019 | Liu | |
| 10,406,034 B2 | 9/2019 | Siegele | |
| 10,426,548 B2 | 10/2019 | Tearney et al. | |
| 10,454,237 B2 | 10/2019 | Yu et al. | |
| 10,456,030 B2 | 10/2019 | Buckland et al. | |
| 10,456,209 B2 | 10/2019 | Peyman | |
| 10,478,060 B2 | 11/2019 | Kubota | |
| 10,493,274 B2 | 12/2019 | Irazoqui et al. | |
| 10,499,809 B2 | 12/2019 | Kalina, Jr. et al. | |
| 10,500,094 B2 | 12/2019 | Buzawa et al. | |
| 10,517,760 B2 | 12/2019 | Berlin | |
| 10,524,822 B2 | 1/2020 | Aljuri et al. | |
| 10,537,476 B2 | 1/2020 | Ha et al. | |
| 10,542,883 B2 | 1/2020 | Gooi et al. | |
| 10,543,122 B2 | 1/2020 | Kahook | |
| 10,543,123 B2 | 1/2020 | Neev | |
| 10,568,763 B2 | 2/2020 | Vera et al. | |
| 10,588,694 B1 | 3/2020 | Neev | |
| 10,596,036 B2 | 3/2020 | Pinchuk | |
| 10,603,214 B2 | 3/2020 | Bigler et al. | |
| 10,603,216 B2 | 3/2020 | Kurtz et al. | |
| 10,653,557 B2 | 5/2020 | Rill et al. | |
| 10,674,906 B2 | 6/2020 | Kalina, Jr. et al. | |
| 10,687,978 B2 | 6/2020 | Berlin | |
| 10,702,416 B2 | 7/2020 | Belkin et al. | |
| 10,744,033 B2 | 8/2020 | Baerveldt et al. | |
| 10,744,034 B2 | 8/2020 | Homer | |
| 10,758,418 B2 | 9/2020 | Vold et al. | |
| 10,765,559 B2 | 9/2020 | Berlin | |
| 10,779,988 B2 | 9/2020 | Fu et al. | |
| 10,799,113 B2 | 10/2020 | Vadakke Matham et al. | |
| 10,821,023 B2 | 11/2020 | Raksi | |
| 10,821,024 B2 | 11/2020 | Raksi | |
| 10,888,461 B2 | 1/2021 | Orthaber et al. | |
| 10,898,381 B2 | 1/2021 | Bendett et al. | |
| 11,019,996 B2 | 6/2021 | Kalina, Jr. et al. | |
| 11,019,997 B2 | 6/2021 | Kalina, Jr. et al. | |
| 11,026,860 B2 | 6/2021 | Andersen et al. | |
| 11,039,958 B2 | 6/2021 | Berlin | |
| 11,110,006 B2 | 9/2021 | Raksi | |
| 11,147,708 B2 | 10/2021 | Horvath et al. | |
| 11,166,630 B2 | 11/2021 | Frisken et al. | |
| 11,173,067 B2 | 11/2021 | Raksi | |
| 11,246,754 B2 | 2/2022 | Holland et al. | |
| 11,316,318 B2 | 4/2022 | Yu et al. | |
| 11,376,160 B2 | 7/2022 | Romano et al. | |
| 11,382,794 B2 | 7/2022 | Sacks et al. | |
| 11,395,765 B2 | 7/2022 | Goldshleger et al. | |
| 11,399,981 B2 | 8/2022 | Fu et al. | |
| 11,583,445 B2 | 2/2023 | Raksi | |
| 11,612,315 B2 | 3/2023 | Delong et al. | |
| 11,759,358 B2 | 9/2023 | Dorin et al. | |
| 11,771,596 B2 | 10/2023 | Belkin et al. | |
| 11,819,457 B2 | 11/2023 | Berlin | |
| 11,826,104 B2 | 11/2023 | Kalina, Jr. et al. | |
| 11,833,079 B2 | 12/2023 | Kim | |
| 11,833,080 B2 | 12/2023 | Hacker et al. | |
| 11,850,186 B2 | 12/2023 | Berlin | |
| 11,857,463 B2 | 1/2024 | Berlin | |
| 11,877,951 B1 | 1/2024 | Junger et al. | |
| 2002/0013572 A1 | 1/2002 | Berlin | |
| 2004/0070761 A1 | 4/2004 | Horvath et al. | |
| 2006/0200113 A1 | 9/2006 | Haffner et al. | |
| 2008/0058781 A1 | 3/2008 | Langeweyde et al. | |
| 2009/0012507 A1 | 1/2009 | Culbertson et al. | |
| 2009/0093798 A1 | 4/2009 | Charles | |
| 2009/0118718 A1 | 5/2009 | Raksi et al. | |
| 2009/0149840 A1 | 6/2009 | Kurtz | |
| 2009/0149841 A1 | 6/2009 | Kurtz | |
| 2009/0157062 A1 | 6/2009 | Hauger et al. | |
| 2009/0185191 A1 | 7/2009 | Boppart et al. | |
| 2010/0130966 A1 | 5/2010 | Brownell | |
| 2010/0324543 A1 | 12/2010 | Kurtz et al. | |
| 2011/0092965 A1 | 4/2011 | Slatkine et al. | |
| 2011/0172649 A1 | 7/2011 | Schuele et al. | |
| 2011/0202046 A1 | 8/2011 | Angeley et al. | |
| 2011/0213664 A1 | 9/2011 | Osterhout et al. | |

(56)  References Cited

U.S. PATENT DOCUMENTS

| | | |
|---|---|---|
| 2011/0214082 A1 | 9/2011 | Osterhout et al. |
| 2011/0282190 A1 | 11/2011 | Caffey et al. |
| 2012/0023557 A1 | 1/2012 | Bevan et al. |
| 2012/0075168 A1 | 3/2012 | Osterhout et al. |
| 2012/0257167 A1 | 10/2012 | Gille et al. |
| 2012/0259321 A1 | 10/2012 | Vera et al. |
| 2012/0283557 A1 | 11/2012 | Berlin |
| 2012/0303007 A1 | 11/2012 | Loesel et al. |
| 2013/0035672 A1 | 2/2013 | Raksi |
| 2013/0085484 A1 | 4/2013 | Van Valen et al. |
| 2013/0103011 A1 | 4/2013 | Grant et al. |
| 2013/0197634 A1 | 8/2013 | Palanker et al. |
| 2013/0226160 A1 | 8/2013 | Rathjen |
| 2013/0237972 A1 | 9/2013 | Raksi |
| 2013/0289450 A1 | 10/2013 | Homer |
| 2014/0128853 A1 | 5/2014 | Angeley et al. |
| 2014/0142599 A1 | 5/2014 | Jeglorz et al. |
| 2014/0216468 A1 | 8/2014 | Goldshleger et al. |
| 2014/0236066 A1 | 8/2014 | Horvath et al. |
| 2014/0288485 A1 | 9/2014 | Berlin |
| 2014/0354951 A1 | 12/2014 | Izatt et al. |
| 2015/0077528 A1 | 3/2015 | Awdeh |
| 2015/0080783 A1 | 3/2015 | Berlin |
| 2015/0157505 A1 | 6/2015 | Neev |
| 2015/0202083 A1 | 7/2015 | Takeda et al. |
| 2015/0297408 A1 | 10/2015 | Dolzan et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0335477 A1 | 11/2015 | Schuele et al. |
| 2015/0359426 A1 | 12/2015 | Buckland et al. |
| 2016/0095751 A1 | 4/2016 | Berlin |
| 2016/0095752 A1 | 4/2016 | Srinivasan et al. |
| 2016/0213512 A1 | 7/2016 | Palanker et al. |
| 2016/0367403 A1 | 12/2016 | Siewert et al. |
| 2017/0020732 A1 | 1/2017 | Berlin |
| 2017/0027437 A1 | 2/2017 | Neal et al. |
| 2017/0042736 A9 | 2/2017 | Berlin |
| 2017/0119579 A9 | 5/2017 | Berlin |
| 2017/0127938 A1 | 5/2017 | Izatt et al. |
| 2017/0202708 A1 | 7/2017 | Berlin |
| 2017/0326003 A1 | 11/2017 | Schuele et al. |
| 2018/0028355 A1 | 2/2018 | Raksi |
| 2018/0207029 A1 | 7/2018 | Herekar et al. |
| 2018/0221205 A1 | 8/2018 | Berlin |
| 2018/0235462 A1 | 8/2018 | Gooi et al. |
| 2018/0360310 A1 | 12/2018 | Berlin |
| 2018/0360655 A1 | 12/2018 | Berlin |
| 2019/0021908 A1 | 1/2019 | Scott |
| 2019/0083313 A1 | 3/2019 | Berlin |
| 2019/0083314 A1 | 3/2019 | Berlin |
| 2019/0117459 A1 | 4/2019 | Berlin |
| 2019/0151146 A1 | 5/2019 | Kim |
| 2019/0240070 A1 | 8/2019 | Schmid et al. |
| 2019/0357768 A1 | 11/2019 | Shareef |
| 2020/0016000 A1 | 1/2020 | Raksi |
| 2020/0016002 A1* | 1/2020 | Raksi ............... A61F 9/00781 |
| 2020/0078216 A1 | 3/2020 | Raksi |
| 2020/0078217 A1 | 3/2020 | Raksi |
| 2020/0078218 A1 | 3/2020 | Holland et al. |
| 2020/0352785 A1 | 11/2020 | Holland et al. |
| 2020/0390605 A1 | 12/2020 | Raksi |
| 2020/0405542 A1 | 12/2020 | Raksi |
| 2021/0022921 A1 | 1/2021 | Berlin |
| 2021/0052416 A1 | 2/2021 | Herekar et al. |
| 2021/0186752 A1 | 6/2021 | Juhasz et al. |
| 2021/0220176 A1 | 7/2021 | Holland et al. |
| 2021/0235986 A1 | 8/2021 | Juhasz et al. |
| 2021/0298945 A1 | 9/2021 | Juhasz et al. |
| 2021/0307964 A1 | 10/2021 | Holland et al. |
| 2021/0315455 A1 | 10/2021 | Delong et al. |
| 2022/0031503 A1 | 2/2022 | Dorin et al. |

FOREIGN PATENT DOCUMENTS

| | | |
|---|---|---|
| DE | 4430720 A1 | 6/1995 |
| EP | 1080706 A1 | 3/2001 |
| EP | 1208792 A1 | 5/2002 |
| EP | 1017308 B1 | 6/2003 |
| EP | 2384727 A1 | 11/2011 |
| JP | 58187911 A | 11/1983 |
| JP | H06319765 A | 11/1994 |
| JP | 2001070337 A | 3/2001 |
| JP | 2005508704 A | 4/2005 |
| JP | 2013255815 A | 12/2013 |
| JP | 2015163193 A | 9/2015 |
| JP | 2016504964 A | 2/2016 |
| JP | 2016105827 A | 6/2016 |
| JP | 2016193033 A | 11/2016 |
| JP | 2019000742 A | 1/2019 |
| KR | 20180008407 A | 1/2018 |
| WO | 2010060443 A1 | 6/2010 |
| WO | 2013188885 A1 | 12/2013 |
| WO | 2017031570 A1 | 3/2017 |
| WO | 2018049246 A1 | 3/2018 |
| WO | 2018073625 A1 | 4/2018 |
| WO | 2018218232 A1 | 11/2018 |
| WO | 2019060756 A1 | 3/2019 |
| WO | 2019173759 A1 | 9/2019 |
| WO | 2020018242 A1 | 1/2020 |
| WO | 2022026239 A1 | 2/2022 |

OTHER PUBLICATIONS

Jones et al., "New methods of measuring the rate of aqueous flow in man with fluorescein". Experimental Eye Research, vol. 5:3, pp. 208-220 (Jul. 1966).

Rosenquist et al., "Ouflow resistance of enucleated human eyes at two different perfusion pressures and different extents of trabeculotomy". Current Eye Research, vol. 8:12, pp. 1233-1240 (1989).

Brubaker, "Goldmann's equation and clinical measures of aqueous dynamics". Experimental Eye Research, vol. 78, Issue 3, pp. 633-637 (2004).

Johnstone, "The aqueous outflow system as a mechanical pump: evidence from examination of tissue and aqueous movement in human and non-human primates". J Glaucoma, vol. 13:5, pp. 421-438 (Oct. 2004).

Dubbelman et al. "The shape of the anterior and posterior surface of the aging human cornea." Vision Research 46 (2006) 9931001. (Jun. 2015).

Hann et al. "Anatomic changes in schlemm's canal and collector channels in normal and primary open-angle glaucoma eyes using low and high perfusion pressures". Glaucoma, vol. 55:9 (Sep. 2014).

Kagemann et al. "Characterisation of Schlemm's canal cross-sectional area." Br J Ophthalmol 2014, 98 (Suppl. II) (Mar. 3, 2014).

Mcnabb et al. "Complete 360 circumferential gonioscopic optical coherence tomography imaging of the iridocorneal angle." Biomedical Optics Express vol. 6, Issue 4, pp. 1376-1391 (2015).

Slobodzian et al. "Apples to Apples: Which Camera Technologies Work Best for Beam Profiling Applications, Part P: Baseline Methods and Mode Effects." Ophir Photonics Group. (2015.

Xin et al. "OCT study of mechanical properties associated with Trabecular meshwork and collector channel motion In human eyes." PLoS One. 2016; 11(9): e0162048. doi: 10.1371/journal.pone.0162048 (Sep. 6, 2016).

Junker et al. "Intraoperative optical coherence tomography and ab interno trabecular meshwork surgery with the trabectome." Clin Ophthalmol. 11: 17551760 (Sep. 28, 2017).

Xin et al. "Aqueous outflow regulation: optical coherence tomography implicates pressure-dependent tissue motion." Experimental Eye Research, vol. 158, pp. 171-186 (May 2017).

International Preliminary Report on Patentability, International Patent Application No. PCT/US2023/027528, Feb. 27, 2025, 12 pgs.

PCT/US2023/027528. International Search Report and Written Opinion (Nov. 27, 2023).

(56)                    References Cited

OTHER PUBLICATIONS

LUMIBIRD; "Optimis™ Fusion Next Generation SLY/YAG Laser";
Quantel Medical; Cournon d'Auvergne, France; 2020; 6 pgs.

* cited by examiner

SYSTEM AND METHOD FOR LASER TREATMENT OF OCULAR TISSUE USING NON-COLLINEAR IMAGING

TECHNICAL FIELD

The present disclosure relates generally to the field of medical devices and treatment of diseases in ophthalmology including glaucoma, and more particularly to systems and methods for laser treatment with non-collinear imaging.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. As shown in FIG. 2, a posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body 6 is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin, porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. With additional reference to FIG. 2, aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due to a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and is directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, and blockage of tissue in the irido-corneal angle 13 along the trabecular outflow pathway 40.

As previously stated, elevated intra-ocular pressure (TOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e., measuring the intra-ocular pressure of the eye, and pachymetry, i.e., measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina.

Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. 12. SLT treatment can be repeated, but subsequent treatments have lower effects on TOP reduction.

ELT uses a 308 nm wavelength ultraviolet (UV) excimer laser and non-thermal interaction with ocular tissue to treat the trabecular meshwork 12 and inner wall of Schlemm's canal 18a in a manner that does not invoke a healing response. Therefore, the TOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of TOP reduction.

SUMMARY

The present disclosure relates to a method of imaging and treating an eye having an optical axis, a cornea, an anterior chamber, and an irido-corneal angle. The method includes delivering an optical coherence tomography (OCT) beam of an OCT imaging apparatus along an OCT optical path that enters a first optical subsystem along an OCT input axis and exits the first optical subsystem along an OCT output axis. The OCT output axis is substantially parallel to the optical axis of the eye, radially offset from the optical axis of the eye, and extends through the cornea and into a portion of the irido-corneal angle at a point along a circumferential angle of the eye. The method further includes imaging the portion of the irido-corneal angle with the OCT beam; delivering a laser beam along an angled optical path through the first optical subsystem, through the cornea, through the anterior chamber, and into a target volume of ocular tissue in the portion of the irido-corneal angle; and photodisrupting at least a portion of the target volume of ocular tissue with the laser beam.

The present disclosure relates to an integrated surgical system that images and treats an eye having an optical axis, a cornea, an anterior chamber, and an irido-corneal angle. The surgical system includes a laser source configured to output a laser beam, an OCT imaging apparatus configured to output an OCT beam, a first optical subsystem configured to couple to the eye, a second optical subsystem optically coupled to the laser source, the OCT imaging apparatus, and the first optical subsystem, and a control system coupled to the laser source, the OCT imaging apparatus, and the second optical subsystem.

The first optical subsystem is configured to receive the OCT beam along an OCT input axis incident to an entry face of the first optical subsystem, and to direct the OCT beam along an OCT optical path through the first optical subsystem to an OCT output axis that: 1) is substantially parallel to the optical axis of the eye, 2) is radially offset from the optical axis of the eye, and 3) extends through the cornea and into a portion of the irido-corneal angle at a point along a circumferential angle of the eye. The first optical subsystem is also configured to receive the laser beam along a laser input axis incident to an entry surface of the first optical subsystem, and to direct the laser beam along an angled optical path 706 through the first optical subsystem 1001, through the cornea, through the anterior chamber, and into a target volume of ocular tissue in the portion of the irido-corneal angle.

The second optical subsystem is configured to deliver the laser beam to the first optical subsystem along the laser input axis, and to deliver the OCT beam to the first optical subsystem along the OCT input axis. The control system is configured to control the OCT imaging apparatus to output the OCT beam to the second optical subsystem, and to image the portion of the irido-corneal angle with the OCT beam, and control the laser source to output the laser beam to the second optical subsystem to photodisrupt at least a portion of the target volume of ocular tissue.

The present disclosure also relates to a focusing objective head configured to couple to a patient interface. The patient interface includes a window that is configured to couple to a cornea of an eye. The focusing objective head includes an exit lens and a prism that is mechanically and optically coupled to the exit lens. The exit lens and prism collectively form an optical assembly that is mechanically secured to a housing of the focusing objective head. The exit lens is configured to optically couple to the window of the patient interface to align an axis of the exit lens with an optical axis of the eye. With reference to FIG. 13a, the optical assembly formed by the exit lens and the prism is configured to receive an OCT beam along an OCT input axis incident to an entry face of the prism, and to direct the OCT beam to an OCT output axis. The OCT output axis is substantially parallel to the axis of the exit lens, is radially offset from the axis of the exit lens, and extends through the exit lens into the cornea and into a portion of the irido-corneal angle of the eye. The optical assembly formed by the exit lens and the prism is also configured to receive a laser beam along a laser input axis incident to an entry surface of the exit lens, and to direct the laser beam along an angled optical path through the exit lens, through the cornea, through the anterior chamber, and into a target volume of ocular tissue in the irido-corneal angle. To this end, the optical assembly formed by the exit lens and the prism includes a reflecting surface arranged to direct the laser beam along the angled optical path.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

Various aspects of systems, apparatuses, and methods will now be presented in the detailed description by way of example, and not by way of limitation, with reference to the accompanying drawings, wherein:

FIGS. 10e1-10e3 are isometric illustrations of an embodiment of a first optical subsystem from different perspectives.

DETAILED DESCRIPTION

Figure 1:
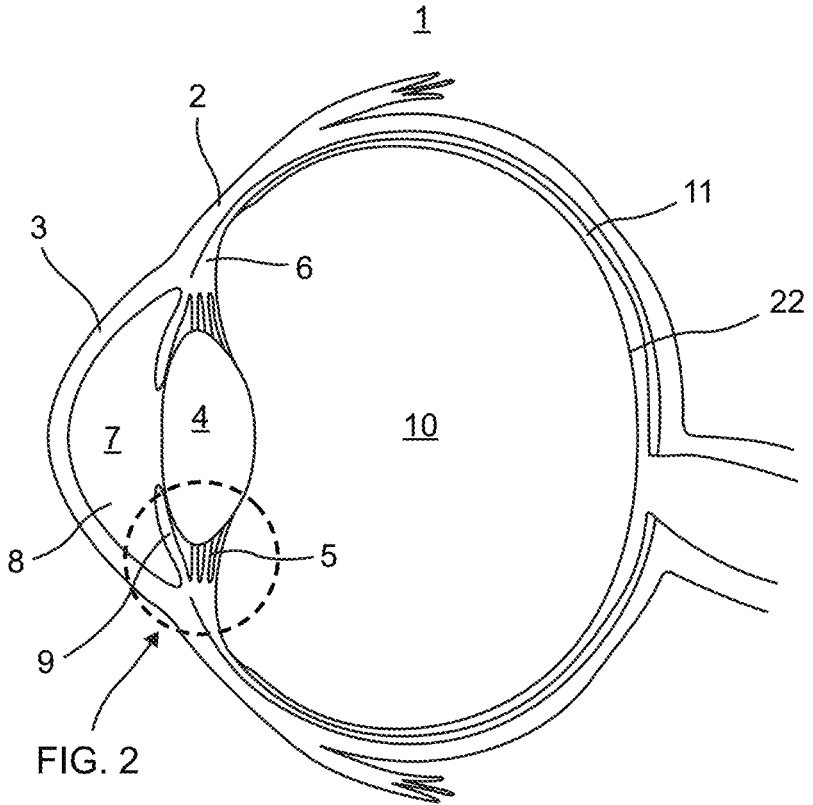
FIG. 1 is a sectional schematic illustration of a human eye and its interior anatomical structures.

An integrated surgical system disclosed herein is configured to image and treat an eye having an optical axis, a cornea, an anterior chamber, and an irido-corneal angle. The system includes a laser source configured to output a laser beam, an OCT imaging apparatus configured to output an OCT beam, a first optical subsystem configured to couple to the eye, a second optical subsystem optically coupled to the laser source, the OCT imaging apparatus, and the first optical subsystem, and a control system coupled to the laser source, the OCT imaging apparatus, and the second optical subsystem.

The first optical subsystem is configured to receive the OCT beam along an OCT input axis incident to an entry face of the first optical subsystem, and to direct the OCT beam to an OCT output axis that: 1) is substantially parallel to the optical axis of the eye, 2) is radially offset from the optical axis of the eye, and 3) extends through the cornea and into a portion of the irido-corneal angle at a point along a circumferential angle of the eye. The first optical subsystem is also configured to receive the laser beam along a laser input axis incident to an entry surface of the first optical subsystem, and to direct the laser beam along an angled optical path through the first optical subsystem, through the cornea, through the anterior chamber, and into a target volume of ocular tissue in the portion of the irido-corneal angle.

The second optical subsystem is configured to deliver the laser beam to the first optical subsystem along the laser input axis, and to deliver the OCT beam to the first optical subsystem along the OCT input axis. The control system is configured to control the OCT imaging apparatus to output the OCT beam to the second optical subsystem, and to image the portion of the irido-corneal angle with the OCT beam, and control the laser source to output the laser beam to the second optical subsystem to photodisrupt at least a portion of the target volume of ocular tissue.

With the integrated surgical system disclosed herein, each of an OCT beam and a laser beam are directed along different optical axes or beam paths into the irido-corneal angle of the eye. The laser beam enters the eye through the cornea, passes through aqueous humor in the anterior chamber and into the irido-corneal angle of the eye where it modifies target ocular tissue. The OCT beam enters the eye from the cornea to the treatment location to image the tissues surrounding the treatment volume directly through the cornea without passing through anterior chamber, thereby avoiding aqueous humor. Accordingly, the by-products of the laser-tissue interaction, e.g., bubbles and/or tissue fragments in aqueous humor, do not block the view of the OCT beam. Also, the OCT beam does not pass through the interface between the trabecular meshwork, cornea, and aqueous humor, and does not suffer aberrations and absorptive losses due to the passage through the interface of the tissues, therefore the quality of the OCT image is better.

Laser surgery procedures for treating glaucoma involve imaging of the irido-corneal angle including the trabecular meshwork. In known laser treatment procedures OCT imaging may be used to identify ocular tissue for treatment. In such procedures, an OCT beam may be delivered colinearly with a laser beam, through common optics and along the same beam path into the irido-corneal angle. During laser treatment, by-products of the laser treatment, such as bubbles and/or tissue fragments from laser photodisruption, can form in the area of the beam path and block the view of a diagnostic OCT beam and thus impact the quality of the OCT images. Furthermore, passage of the OCT beam through various tissue interfaces may result in aberrations and absorptive losses that affect the quality of the OCT images. Another drawback of delivering an OCT beam colinearly with a laser beam is the inability to acquire OCT images that resolve deep enough to identify clinically important features such as Schlemm's canal. This lack of depth penetration may limit the clinical utility of the OCT images.

The integrated surgical system disclosed herein directs OCT beams into the eye in a way that avoids by-products of laser treatment and optical aberrations and absorptions by tissues of the eye to thereby provide quality OCT imaging.

Femtosecond Laser Source

A surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for breaking up the interior of the crystalline lens to smaller fragments to facilitate extraction. Entry incisions through the cornea opens the eye for access with manual surgical devices and for insertions of phacoemulsification devices and intra-ocular lens insertion devices. Several companies have commercialized such surgical systems, among them the IntraLase system now available from Johnson & Johnson Vision, Santa Ana, CA, the LenSx and WaveLight systems from Alcon, Fort Worth, TX, the Lensar Laser System from Lensar, Inc., Orlando FL; the family of Femto Lasers from Ziemer Ophthalmics, Alton IL; the Victus Femtosecond Laser Platform from Bausch and Lomb, Rochester, NY; and the Catalys Precision Laser System from Johnson & Johnson, Santa Ana, CA.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis 24 to the eye 1, is not appropriate for reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In accordance with the integrated surgical system disclosed herein, access to the irido-corneal angle 13 for purposes of laser treatment is provided along an angled beam path 30 that is at an angle relative to the optical axis 24 to the eye 1. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above-mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, CA, Coherent, Santa Clara, CA, Amplitude Systems, Pessac, France, NKT Photonics, Birkerod, Denmark, and other vendors.

OCT Imaging

Figure 2:
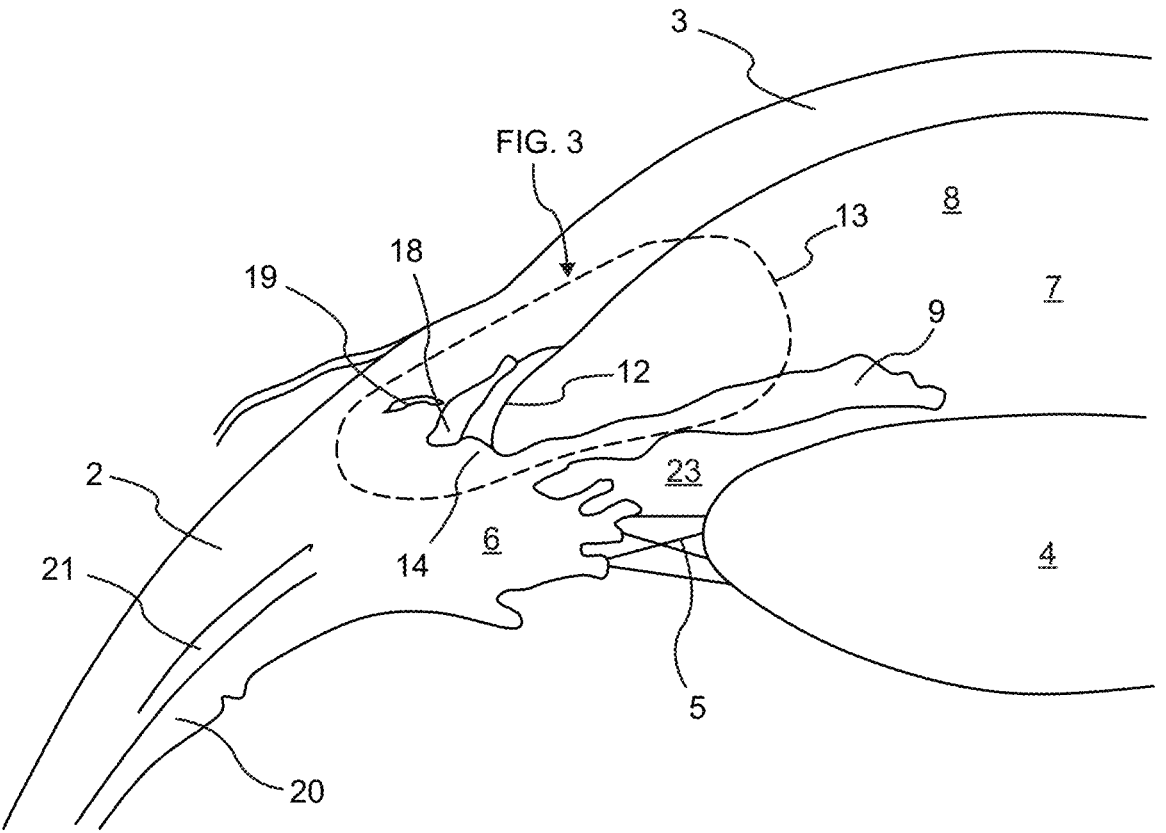
FIG. 2 is a sectional schematic illustration of the irido-corneal angle of the eye of FIG. 1.
Figure 3:
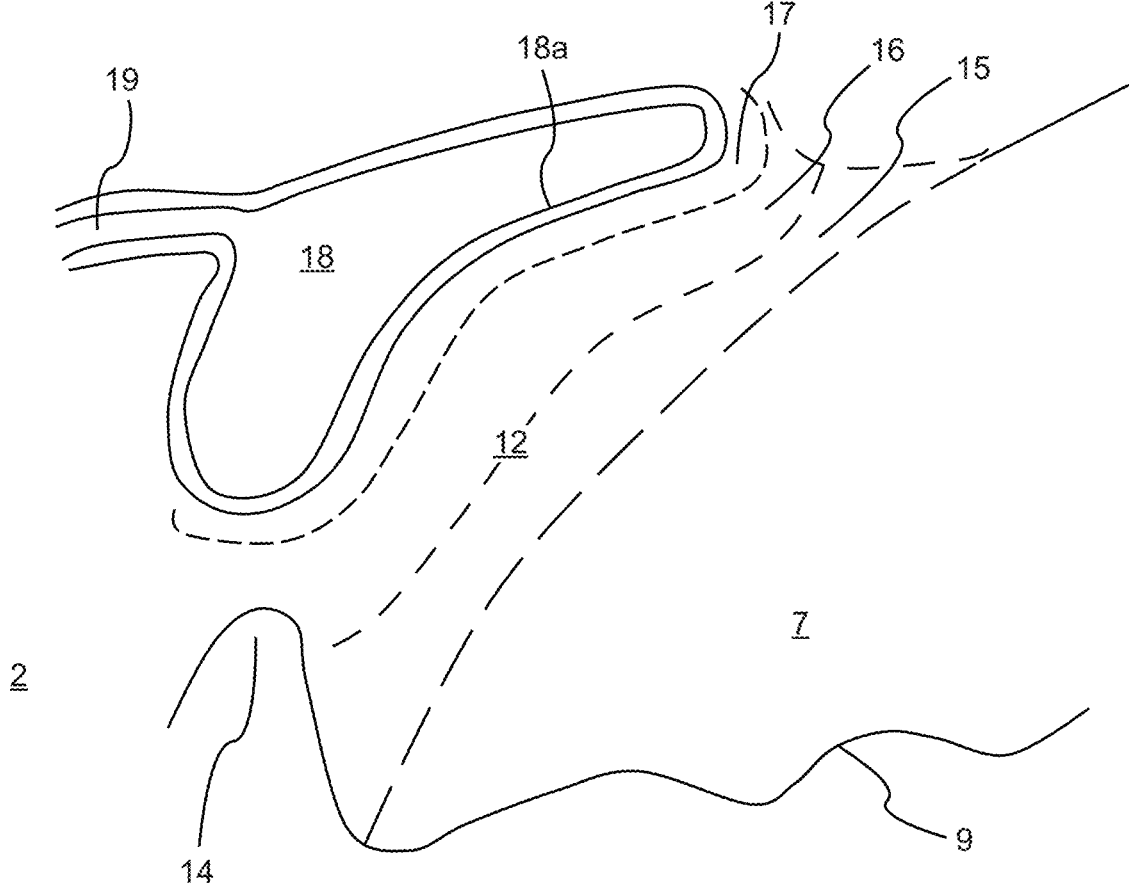
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
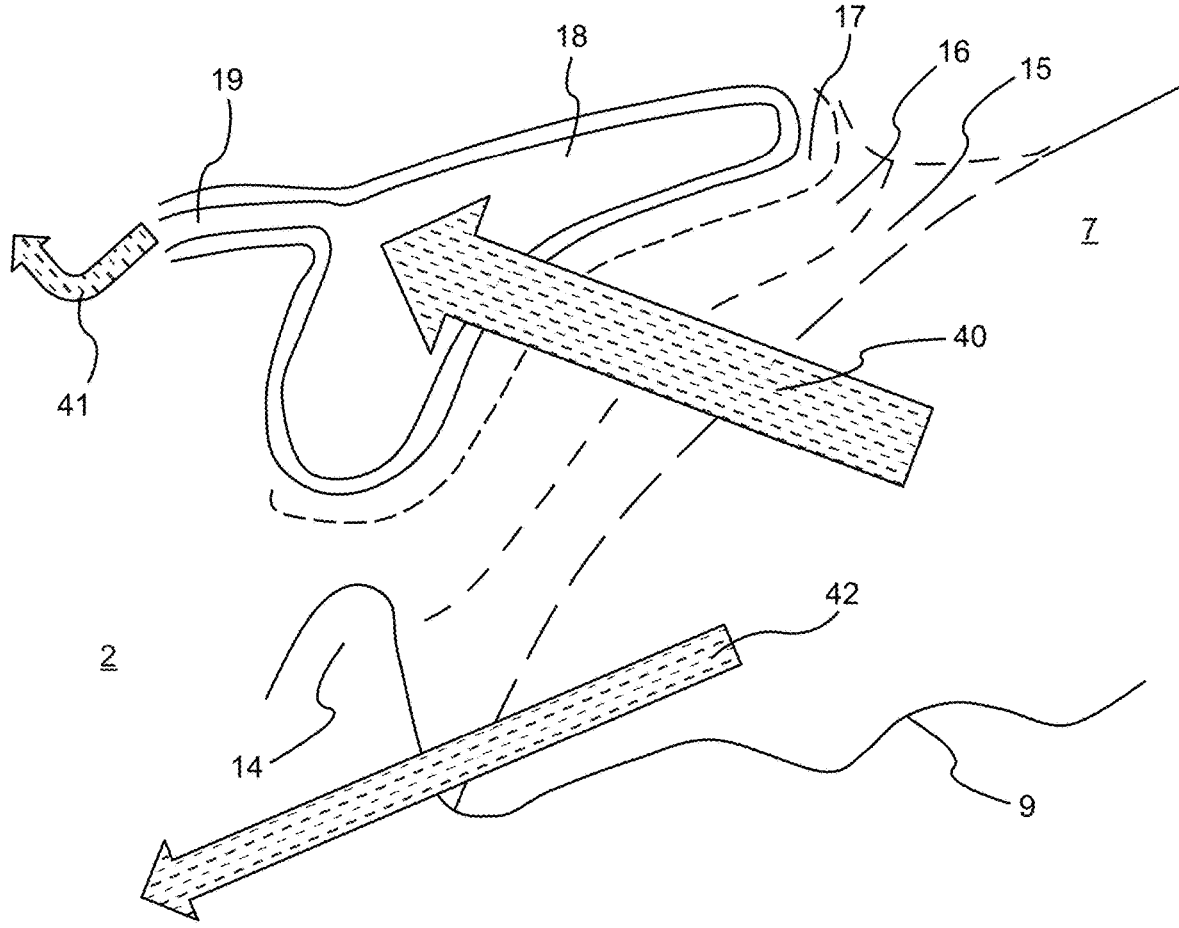
FIG. 4 is a sectional schematic illustration of various outflow pathways for aqueous humor through the trabecular meshwork, Schlemm's canal, and collector channels of FIG. 3.
Figure 5:
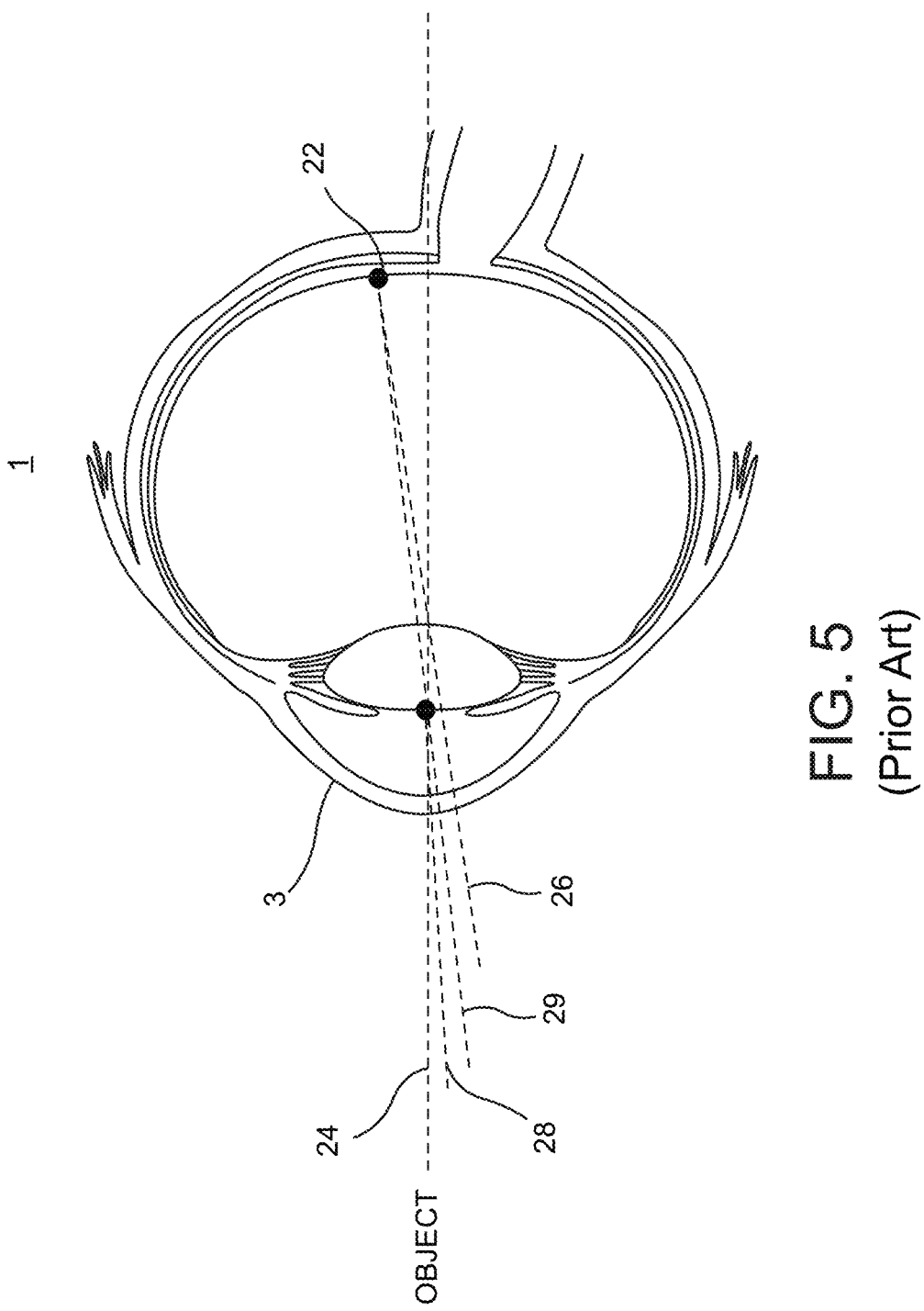
FIG. 5 is a sectional schematic illustration of a human eye showing various axes associated with the eye.

An imaging component of the integrated surgical system disclosed herein is an OCT imaging apparatus. OCT technology may be used to diagnose, locate, and guide laser surgery directed to the irido-corneal angle of the eye. For example, with reference to FIGS. 1-3, OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

In accordance with the integrated surgical system disclosed herein, access to the irido-corneal angle 13 for purposes of OCT imaging is provided along a parallel beam path 31 that is substantially parallel to the optical axis 24 to the eye 1. OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape, and location of structures in the eye for surgical targeting. It is also possible to reconstruct three-dimensional (3D) images from a multitude of 2D cross-sectional images but often it is not necessary. Acquiring, analyzing, and displaying 2D images is faster and can still provide all information necessary for precise surgical targeting.

OCT is an imaging modality capable of providing high resolution images of materials and tissue. Imaging is based on reconstructing spatial information of the sample from spectral information of scattered light from within the sample. Spectral information is extracted by using an interferometric method to compare the spectrum of light entering the sample with the spectrum of light scattered from the sample. Spectral information along the direction that light is propagating within the sample is then converted to spatial information along the same axis via the Fourier transform. Information lateral to the OCT beam propagation is usually collected by scanning the beam laterally and repeated axial probing during the scan. 2D and 3D images of the samples can be acquired this way. Image acquisition is faster when the interferometer is not mechanically scanned in a time domain OCT, but interference from a broad spectrum of light is recorded simultaneously. This implementation is called a spectral domain OCT. Faster image acquisition may also be obtained by scanning the wavelength of light rapidly from a wavelength scanning laser in an arrangement called a swept-source OCT.

The axial spatial resolution limit of the OCT is inversely proportional to the bandwidth of the probing light used. Both spectral domain and swept source OCTs are capable of axial spatial resolution below 5 micrometers ($\mu$m) with sufficiently broad bandwidth of 100 nanometers (nm) or more. In the spectral domain OCT, the spectral interference pattern is recorded simultaneously on a multichannel detector, such as a charge coupled device (CCD) or complementary metal oxide semiconductor (CMOS) camera, while in the swept source OCT the interference pattern is recorded in sequential time steps with a fast optical detector and electronic digitizer. There is some acquisition speed advantage of the swept source OCT but both types of systems are evolving and improving rapidly, and resolution and speed is sufficient for purposes of the integrated surgical system disclosed herein. Stand-alone OCT systems and OEM components are now commercially available from multiple vendors, such as Optovue Inc., Fremont, CA, Topcon Medical Systems, Oakland, NJ, Carl Zeiss Meditec AG, Germany, Nidek, Aichi, Japan, Thorlabs, Newton, NJ, Santec, Aichi, Japan, Axsun, Billercia, MA, and other vendors.

Visual Observation Apparatus

Another imaging component of the integrated surgical system disclosed herein is a visual observation apparatus. The visual observation apparatus may include, for example, a video camera, a telescope, and one or more illumination sources. The camera may be a digital camera fitted with a goniolens to provide gonioscopic images of the eye. The illumination sources are positioned for optimal irradiance of the object of interested, e.g., the irido-corneal angle of the eye including in particular, the trabecular meshwork. Illumination sources may be LEDs or light delivered via fiber optic cables. Illumination schemes are numerous: refractive ballistic schemes where the sources are placed in air and light refracts through the optics to reach the trabecular meshwork; transmissive ballistic schemes where illumination sources are inserted into pre-drilled holes or features inside lenses and adhered using index-matched epoxy; or reflective schemes where light from illumination sources strikes the trabecular meshwork after reflecting off designed reflective surfaces on lenses close to the eye.

Accessing the Irido-Corneal Angle

With reference to FIGS. 6, 7, 8, and 13a, a feature provided by the integrated surgical system 1000 disclosed herein is access to the targeted ocular tissue in the irido-corneal angle 13 by different light beams along different, non-colinear beam paths 30, 31. In some embodiments, the irido-corneal angle 13 of the eye may be accessed by one or more beams via the integrated surgical system along a first beam path 30 passing through the cornea 3 and through the aqueous humor 8 in the anterior chamber 7, while one or more other beams may access the irido-corneal angle 13 along a second beam path 31 passing through the cornea 3 and into the irido-corneal angle 13 of the eye without passing through the aqueous humor 8 in the anterior chamber 7. For example, one or more of a laser beam and a visual observation beam may access the irido-corneal angle 13 of the eye along the first beam path 30, while an OCT beam accesses the irido-corneal angle 13 of the eye along the second beam path 31. The first beam path 30 is at an angle relative to the optical axis 24 of the eye and is thus referred to herein as an angled beam path or angled optical path. The second beam path 31 is substantially parallel to the optical axis 24 and is thus referred to herein as a parallel beam path or parallel optical path. Substantially parallel means within 20 degrees of parallel.

Figure 6:
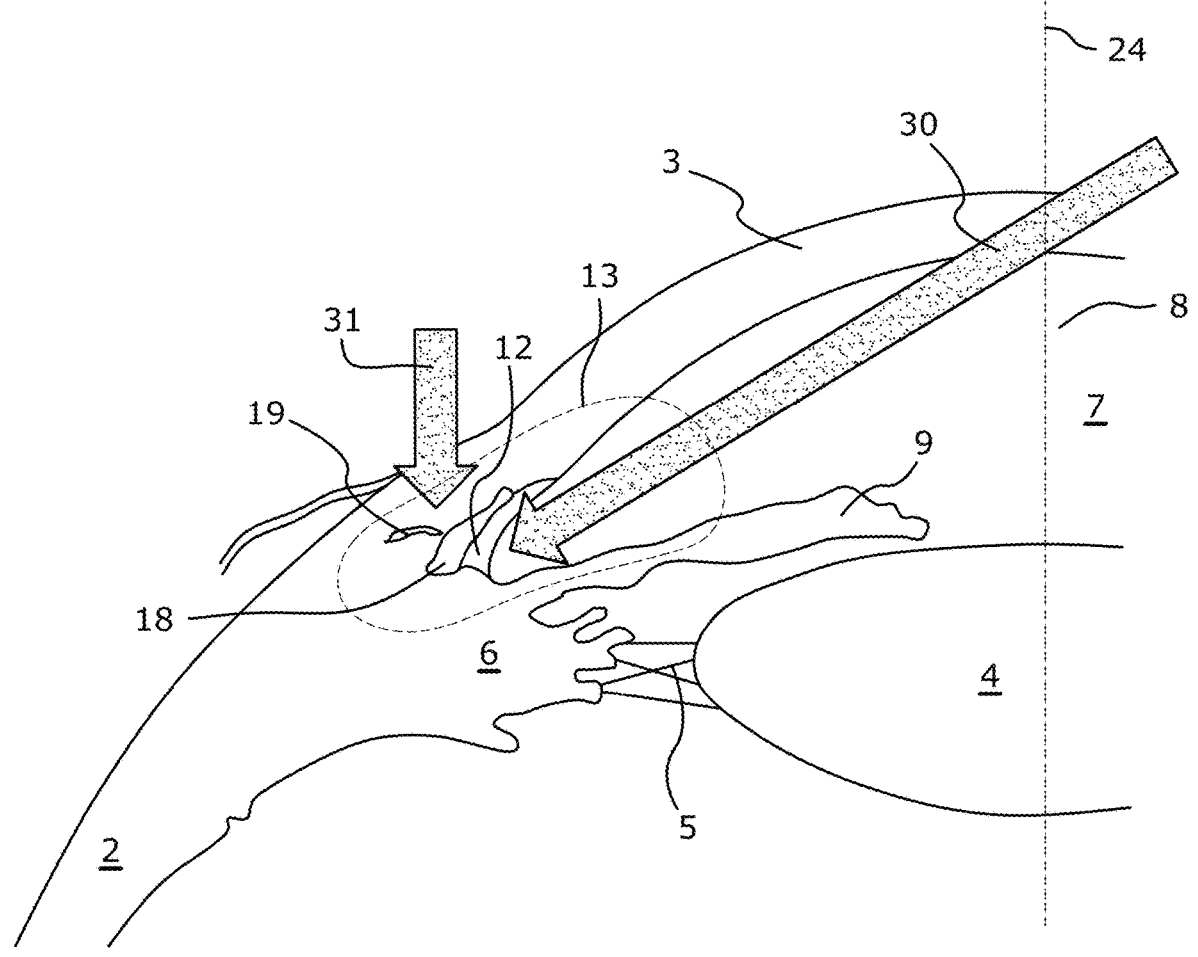
FIG. 6 is a sectional schematic illustration of two different beam paths, including an angled beam path and a parallel beam path, along which one or more light beams may access the irido-corneal angle of the eye.
Figure 13A:
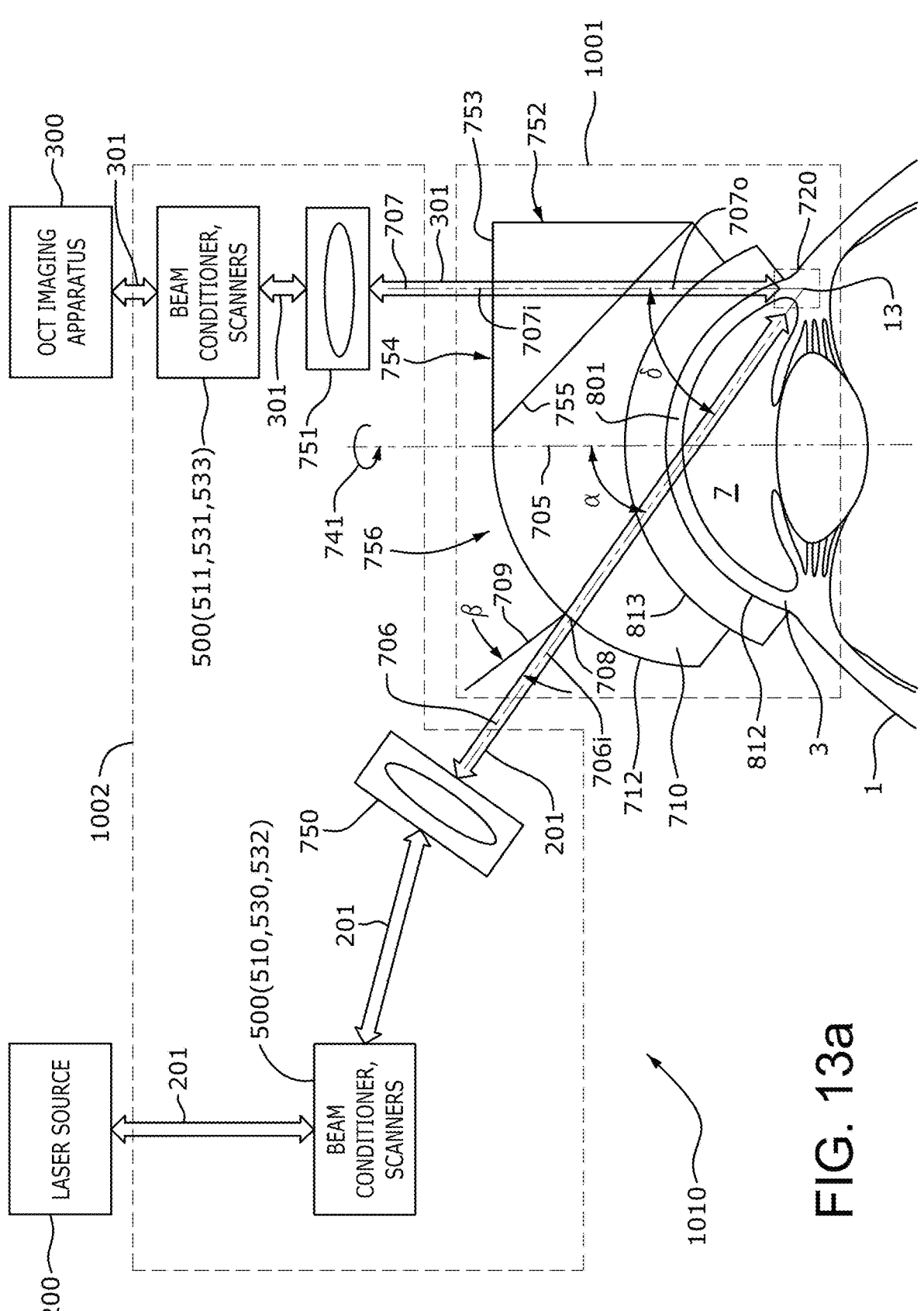
FIG. 13a is a schematic illustration of components of the integrated surgical system of FIGS. 7 and 8 functionally arranged to form a first optical subsystem and a second optical subsystem that enable access to the irido-corneal angle along each of the angled beam path and the parallel beam path of FIG. 6.

With reference to FIG. 13a, an optical system 1010 disclosed herein is configured to direct a first light beam, e.g., a laser beam 201, to an irido-corneal angle 13 of an eye along the angled beam path 30 (shown in FIG. 6) while also directing a second light beam, e.g., an OCT beam 301, to the irido-corneal angle 13 along the parallel beam path 31 (shown in FIG. 6). The optical system 1010 includes a first optical subsystem 1001 and a second optical subsystem 1002.

Continuing with FIG. 13a, the first optical subsystem 1001 includes an exit lens 710, a prism 752, and a window 801. The exit lens 710 (also referred to as the superdome) has opposed input and output sides. The input side of the exit lens 710 is defined by a convex surface and the output side is defined a concave surface. The input side of the exit lens 710 is arranged to receive a first light beam, e.g., a laser beam. The prism 752 has a flat input surface arranged to receive the second light beam, e.g., OCT beam, and an output surface configured to couple with a section of the convex surface of the exit lens 710.

The window 801 has opposed input and output sides. The input side of the window 801 is defined by a convex surface and the output side is defined a concave surface. The concave surface of the window 801 is configured to couple to the convex surface of the exit lens 710 to define a first optical axis 705 (also referred to herein simply as an "axis," or a "first optical subsystem axis" or just a "subsystem axis") extending through the window and the exit lens. The concave surface of the window 801 is configured to detachably couple to a cornea 3 of the eye 1 such that when coupled to the eye, the first optical axis is generally aligned with the direction of view of the eye or the optical axis 24 of the eye.

Continuing with FIGS. 6 and 13a, the second optical subsystem 1002 is configured to output one or more first light beams, e.g., a laser beam 201 and/or a visual observation beam 401, into the first optical subsystem 1001 for travel along the first beam path 30. The second optical subsystem 1002 is also configured to output a second light beam, e.g., OCT beam 301, into the first optical subsystem 1001 for travel along the second beam path 31.

Regarding the first light beam, the optical system 1010 is configured so that the first light beam, e.g., a laser beam 201 and/or visual observation beam 401, is directed to be incident at the convex surface of the exit lens 710 along a laser axis 706 at an angle α that is offset from the first optical subsystem axis 705. The respective geometries and respective refractive indices of the exit lens 710 and window 801 are configured to compensate for refraction and distortion of the light beam by bending the light beam so that it is directed through the cornea 3 of the eye toward the irido-corneal angle 13. More specifically, the first optical subsystem 1001 bends the beam so that the first light beam, e.g., laser beam 201, exits the first optical subsystem and enters the cornea 3 at an appropriate angle so that the beam progresses through the cornea and the aqueous humor 8 of the anterior chamber 7 in a direction along the angled beam path 30 toward the irido-corneal angle 13.

With reference to FIG. 6, accessing the irido-corneal angle 13 along the angled beam path 30 provides several advantages. An advantage of this angled beam path 30 to the irido-corneal angle 13 is that the light beam passes through mostly clear tissue, e.g., the cornea 3 and the aqueous humor 8 in the anterior chamber 7. Thus, scattering of the beam by tissue is not significant. This is beneficial when the light beam is a laser beam or a visual observation beam. An additional advantage of the angled beam path 30 to the irido-corneal angle 13 through the cornea 3 and the anterior chamber 7 is the avoidance of direct laser beam illuminating the retina 11. As a result, higher average power laser light can be used for imaging and surgery, resulting in faster procedures and less tissue movement during the procedure.

Continuing with FIGS. 6 and 13*a*, regarding the second light beam, the optical system 1010 is configured so that the second light beam, e.g., OCT beam 301, is directed to be incident at the flat input surface of the prism 752 along an OCT axis 707 that is radially offset from the subsystem axis 705 and has a direct path to the irido-corneal angle of the eye. The respective geometries and respective refractive indices of the prism 752, the exit lens 710, and the window 801 are configured to compensate for refraction and distortion of the OCT beam by bending the OCT beam so that it is directed through the cornea 3 of the eye toward the irido-corneal angle 13. More specifically, the first optical subsystem 1001 directs the OCT beam 301 so that the OCT beam exits the first optical subsystem and enters the cornea 3 at an appropriate angle so that the OCT beam progresses through the cornea in a direction along the parallel beam path 31 toward the irido-corneal angle 13 while avoiding the anterior chamber 7.

As noted above, providing OCT beam access to the irido-corneal angle 13 along the parallel beam path 31 that is separate from the angled beam path 30 of the laser beam provides several advantages. For example, the parallel beam path 31 of the OCT beam avoids by products of laser treatment that may be in the area of the angled beam path 30. The parallel beam path 31 also avoids and optical aberrations and absorptions at tissue interfaces of the eye, e.g., the cornea to aqueous humor interface, and the aqueous humor to trabecular meshwork interface. Avoidance of these optical aberrations and absorptions: 1) provide higher OCT resolution and contrast, and higher sensitivity, 2) enable deeper penetration of the OCT beam to the tissues, resulting in full view of the vicinity of the Schlemm's canal and collector channels, and 3) allows the use of less OCT beam power and the use of different wavelength for the OCT.

Providing OCT beam access to the irido-corneal angle 13 along the parallel beam path 31, apart from the angled beam path 30 of the laser beam allows the OCT beam access to, and the identification and targeting of, a various tissues in the periphery of the cornea for laser treatment. For example, it allows imaging of and targeted treatment of not only the trabecular meshwork, but also the Schlemm's canal, collector channels, aqueous veins, and scleral tissue. Providing OCT beam access to the irido-corneal angle 13 along the parallel beam path 31, apart from the angled beam path 30 of the laser beam also provides the ability to image the tissue during and immediately after surgical laser treatment, to thereby obtain direct feedback of surgical performance during and after treatment. OCT beam access to the irido-corneal angle 13 along the parallel beam path 31 also provides better images for treatment planning prior to surgery. Separating the OCT beam path from the laser beam path also allows optimization of each beam for less aberrations, less chromatic dispersion, and independent polarization alignment.

Having thus generally described the integrated surgical system 1000 and some of its features and advantages, a more detailed description of the system and its component parts follows.

Integrated Surgical System

Figure 7:
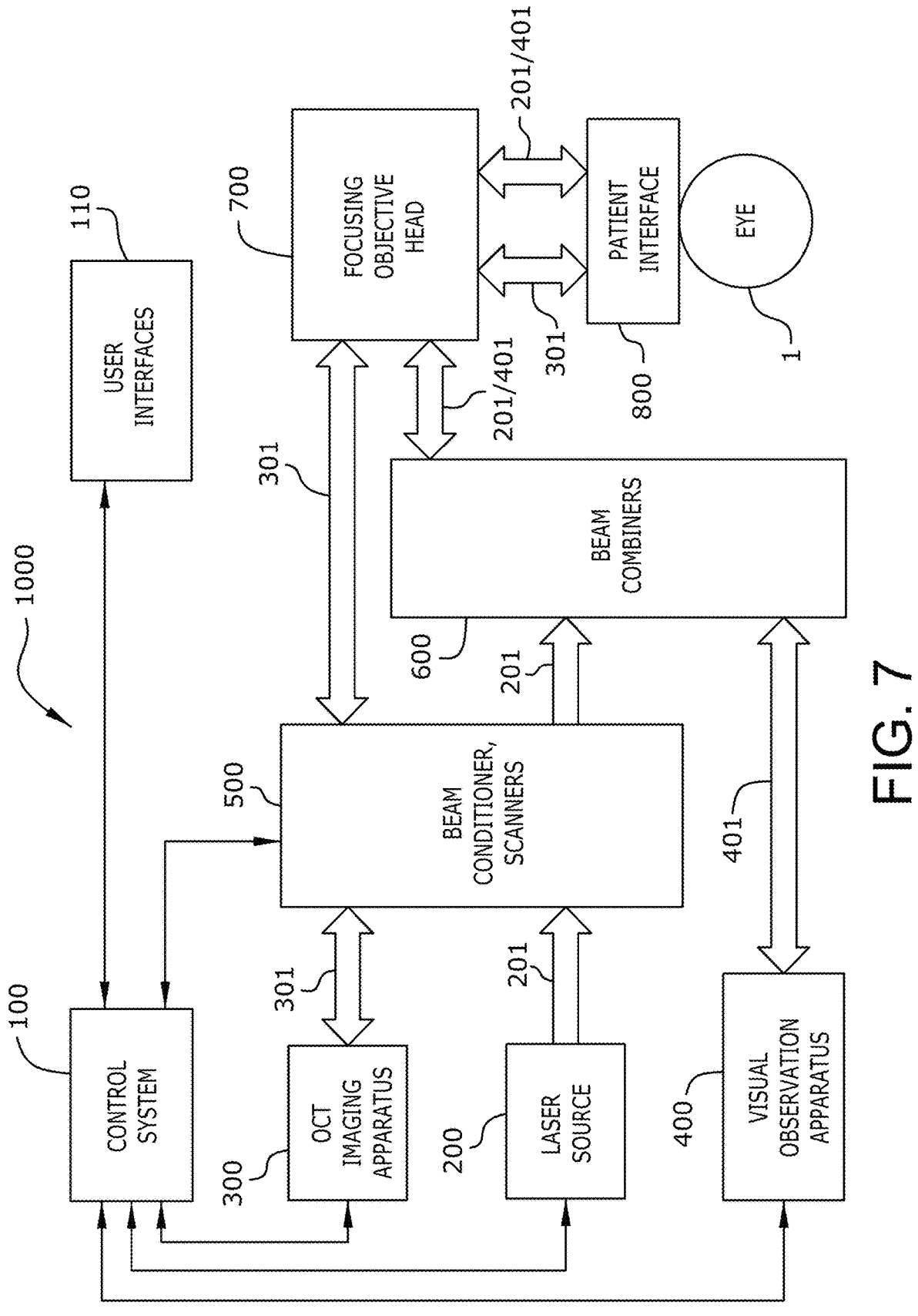
FIG. 7 is a block diagram of an integrated surgical system for non-invasive glaucoma surgery including a control system, a laser source, an OCT imaging apparatus, a visual observation apparatus, beam conditioners and scanners, beam combiners, a focusing objective head, and a patient interface.

With reference to FIG. 7, an integrated surgical system 1000 for non-invasive glaucoma surgery includes a control system 100, a surgical component 200, a first imaging component 300, and an optional second imaging component 400. In the embodiment of FIG. 7, the surgical component 200 is a femtosecond laser source, the first imaging component 300 is an OCT imaging apparatus, and the optional second imaging component 400 is a visual observation apparatus, e.g., a microscope with an illumination source, for direct viewing or viewing with a camera. The visual observation apparatus 400 provides visual illumination and observation that assists the surgeon in docking the eye to the system. The visual observation apparatus 400, together with the OCT imaging apparatus 300, provide imagery that assist in identifying surgical locations. Other components of the integrated surgical system 1000 include beam conditioners and scanners 500, beam combiners 600, a focusing objective head 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye 1 to the system 1000, selection of pre-programmed or live generated surgical plans, defining surgical location based on images of the eye, including visual observation and OCT images, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, including visual observation and OCT images, graphical, numerical, and textual display of the surgical plan and the progress of the surgery.

The control system 100 is connected to the other components 200, 300, 400, 500 of the integrated surgical system 1000. Control signals from the control system 100 to the femtosecond laser source 200 function to control internal and external operation parameters of the laser source, including for example, power, repetition rate and beam shutter. Control signals from the control system 100 to the OCT imaging apparatus 300 function to control OCT beam parameters, and the acquiring, analyzing, and displaying of OCT images. Control signals to the laser scanning system may include location, size and shape of surgical patterns expressed in position coordinates of the intended location of focus of the laser and the scanning path of the laser across the surgical volume. These types of control signals can be pre-programmed, with one or more control parameters selectable by the operator. The control parameters of the surgical pattern may include the location of the pattern, the shape, length, width and depth of the pattern, laser spot, line and layer separation and energy of the laser pulses. Control signals to and from various subsystems and components are calibrated prior to operating the surgical system. The calibration includes calibrating the pixel coordinates acquired and displayed by the visual observation apparatus 400 and the OCT imaging apparatus 300 to actual physical coordinates in the eye and includes calibrating commanded motions of the OCT and laser scanner systems to actual OCT and laser beam displacements in the eye.

Commanding the integrated surgical system 1000 to make a surgical incision includes docking the system on the eye, acquiring, and displaying visual observation images and OCT images on a computer screen, determining the coordinate location and other parameters of the intended surgical incision based on the displayed images and instructing the control system 100 to execute the surgical pattern based on information collected from those images. The parameters based on the images may be determined by the operator of the integrated surgical system 1000 or may be determined by an image processing and analyzing computer algorithm. Instructions using these parameters can be given by the operator as entering input data in the form of text, mouse clicks and drag and drop commands on the computer screen. Alternatively, a system processor that may be included in the control system 100 generates instructions for execution by the control system based on the previously determined parameters.

Laser beams 201 from the femtosecond laser source 200 and OCT beams 301 from the OCT imaging apparatus 300 are directed towards a unit of beam conditioners and scanners 500. The beam conditioners and scanners 500 include components, e.g., scanning mirrors, for scanning the laser beams 201 and OCT beams 301 independent of each other. Different kind of scanners can be used for the purpose of scanning the laser beam 201 and the OCT beam 301. For scanning transversal to a beam 201, 301, angular scanning galvanometer scanners are available for example from Cambridge Technology, Bedford, MA, Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective head 700. Therefore, beam conditioners are applied before, after, or in between individual scanners. The beam conditioner and scanners 500 includes scanners for scanning a beam transversally and axially. Axial scanning changes the depth of the focus at the target region. Axial scanning can be performed by moving a lens axially in the beam path with a servo or stepper motor.

The laser beam 201 and the visual observation beam 401 are combined with dichroic, polarization or other kind of beam combiners 600 to reach a common target volume or surgical volume in the eye. The beam combiner 600 uses dichroic or polarization beam splitters to split and recombine light with different wavelength and/or polarization. The beam combiner 600 may also include optics to change certain parameters of the individual beams 201, 401 such as beam size, beam angle and divergence.

To resolve ocular tissue structures of the eye in sufficient detail, the imaging components 300, 400 of the integrated surgical system 1000 may provide an OCT beam 301 and a visual observation beam 401 having a spatial resolution of several micrometers. The resolution of the OCT beam 301 is the spatial dimension of the smallest feature that can be recognized in the OCT image. It is determined mostly by the wavelength and the spectral bandwidth of the OCT source, the quality of the optics delivering the OCT beam 301 to the target location in the eye, the numerical aperture of the OCT beam and the spatial resolution of the OCT imaging apparatus at the target location. In one embodiment, the OCT beam 301 of the integrated surgical system 1000 has a resolution of no more than 5 μm.

Likewise, the surgical laser beam 201 provided by the femtosecond laser source 200 may be delivered to targeted locations with several micrometer accuracy. The resolution of the laser beam 201 is the spatial dimension of the smallest feature at the target location that can be modified by the laser beam without significantly affecting surrounding ocular tissue. It is determined mostly by the wavelength of the laser beam 201, the quality of the optics delivering the laser beam to target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 μm.

It should be noted that, while the visual observation beam 401 is acquired by the visual observation apparatus 400 using fixed, non-scanning optics, the OCT beam 301 of the OCT imaging apparatus 300 is scanned laterally in two transversal directions. The laser beam 201 of the femtosecond laser source 200 is scanned in two lateral dimensions and the depth of the focus is scanned axially.

For practical embodiments, beam conditioning, scanning, and combining the optical paths are certain functions performed on the laser, OCT, and visual observation optical beams. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulate different beams. In the embodiment disclosed herein, the beam conditioners and scanners 500 include two sets of scanners, one for scanning the laser beam 201 and the other for scanning the OCT beam 301. Separate beam conditioners within the beam conditioners and scanners 500 set respective beam parameters for the laser beam 201 and the OCT beam 301. While many combinations of optical hardware arrangements are possible for the integrated surgical system, the following section describes in detail an example arrangement.

Beam Delivery

In the following description, the term "beam" may—depending on the context—refer to one of a laser beam, an OCT beam, an illumination beam, or a visual observation beam. The term "colinear beams" refers to two or more different beams that are combined by optics of the integrated surgical system 1000 to share a same path to a same target location of the eye as they enter the eye. The term "non-colinear beams" refers to two or more different beams that have different paths into the eye. The term "co-targeted beams" refers to two or more different beams that have different paths into the eye but that target a same location of the eye. In colinear beams, the different beams may be combined to share a same path into the eye by dichroic or polarization beam splitters, and delivered along a same optical path through a multiplexed delivery of the different beams. In non-colinear beams, the different beams are delivered into the eye along different optical paths that are separated spatially or by an angle between them. In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus, an OCT beam output by the OCT imaging apparatus moves in the distal direction toward the eye. The proximal direction refers to a direction away from the eye; thus, an OCT return beam from the eye moves in the proximal direction toward the OCT imaging apparatus.

Figure 8:
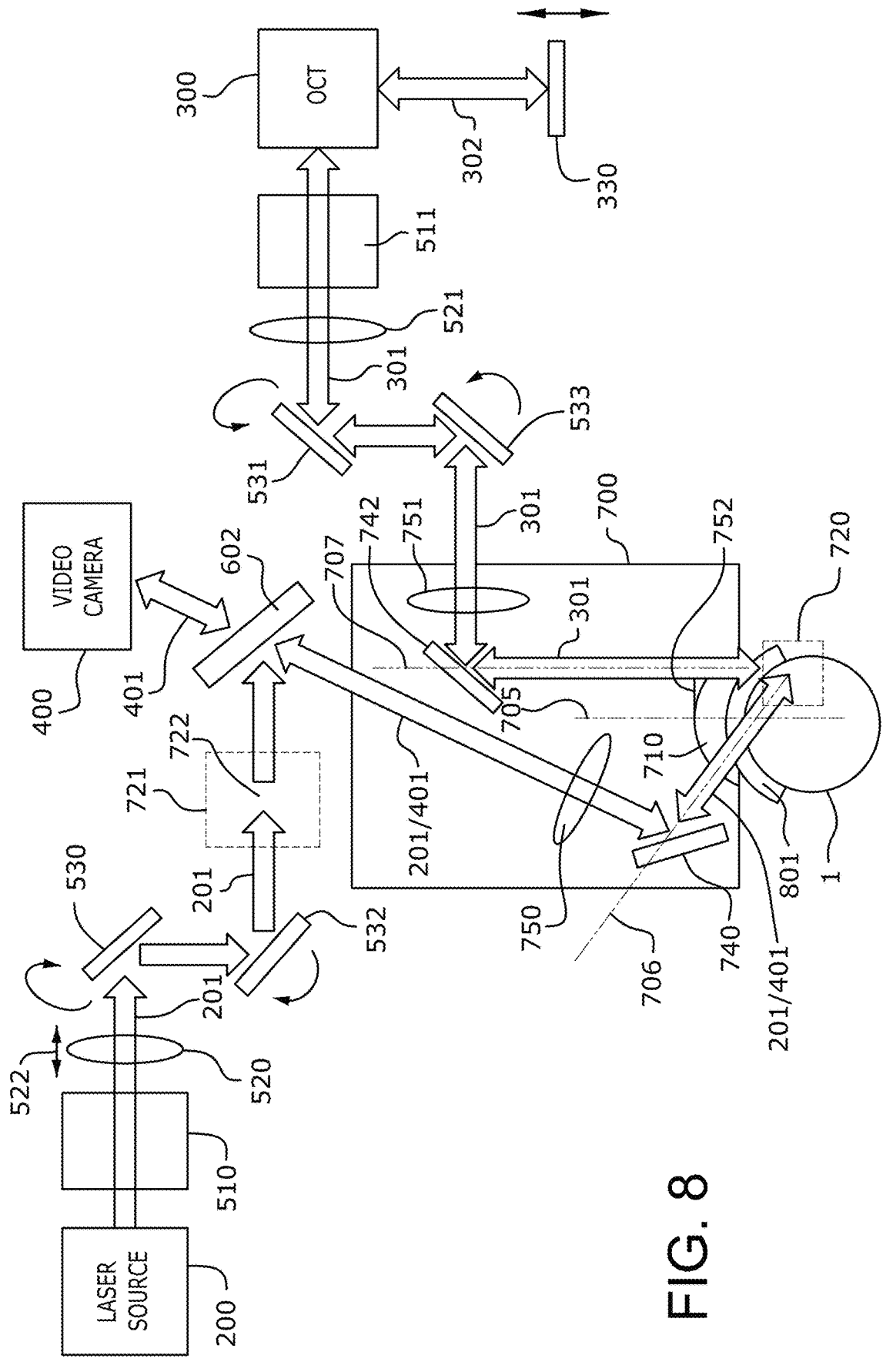
FIG. 8 is a detailed block diagram of the integrated surgical system of FIG. 7.

Referring to FIG. 8, and in accordance with embodiments disclosed herein, an integrated surgical system is configured to deliver each of a laser beam 201, an OCT beam 301, and a visual observation beam 401 in the distal direction toward an eye 1, and receive each of an OCT return beam and a visual observation return beam back from the eye 1. The laser beam 201 and the visual observation beam 401 are delivered along a first optical path or angled beam path into a region of the eye 1 that includes a surgical volume 720, while the OCT beam 301 is delivered along a second optical path or parallel beam path into the same region of the eye. The laser beam 201 and the OCT beam 301 are thus co-targeted, non-colinear beams.

Regarding visual observation, the visual observation beam 401 directed toward the eye is a light beam from an illumination source of the visual observation apparatus, and the visual observation return beam back from the eye 1 is a reflection of that light beam.

Regarding the delivery of a laser beam, a laser beam 201 output by the femtosecond laser source 200 passes through a beam conditioner 510 where the basic beam parameters, beam size, divergence are set. The beam conditioner 510 may also perform additional functions, such as setting the beam power or pulse energy and shuttering the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

An intermediate focal point 722 is set to fall within, and is scannable in, the conjugate surgical volume 721, which is an image conjugate of the surgical volume 720, determined by the focusing objective head 700. The surgical volume 720 is the spatial extent of the region of interest within the eye where imaging and surgery is performed. For glaucoma surgery, the surgical volume 720 is the vicinity of the irido-corneal angle 13 of the eye. A pair of transverse scanning mirrors 530, 532 rotated by a galvanometer scanner scan the laser beam 201 in two essentially orthogonal transversal directions, e.g., in the x and y directions. Then the laser beam 201 is directed towards a beam combining mirror 602 configured to combine the laser beam 201 with a visual observation beam 401.

The combined laser/visual beam 201/401 traveling in the distal direction then passes through a focusing lens 750 included in the focusing objective head 700, is reflected by a reflecting surface 740, which may be a planar beam-folding mirror or a facet inside an optic, and then passes through an exit lens 710 of the focusing objective head 700 and a window 801 of a patient interface, where the intermediate focal point 722 of the laser beam within the conjugate surgical volume 721 is re-imaged into a focal point in the surgical volume 720. The focusing objective head 700 re-images the intermediate focal point 722, through the window 801 of a patient interface, into the ocular tissue within the surgical volume 720. In one configuration, the reflecting surface 740 in the form of a facet inside an optic may have a specialized coating for broadband reflection (visible, OCT and femtosecond) and low difference between s and p polarization group delay dispersion (GDD).

Regarding delivery of an OCT beam, an OCT beam 301 output by the OCT imaging apparatus 300 passes through a beam conditioner 511, an axially moveable focusing lens 521 and a transversal scanner with scanning mirrors 531, 533. The focusing lens 521 is used to set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302.

However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 passes through a OCT focusing lens 751 included in the focusing objective head 700 and is reflected by a reflecting surface 742 (also referred to herein as an "OCT mirror"), which may be a planar beam-folding mirror or a facet inside an optic. Continuing in the distal direction, the OCT beam 301 then passes through the prism 752 and the exit lens 710 of the focusing objective head 700, and the window 801 of a patient interface 800 into a focal point in the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a moveable mirror 330. The reference beam 302 is combined interferometrically with the OCT return beam 301 on its return within the OCT imaging apparatus 300. The amount of delay in the reference delay optical path is adjustable by moving the moveable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the laser beam 201 is delivered through the cornea 3 and the anterior chamber 7, the beam passes through posterior and anterior surface of the cornea at a steep angle, far from normal incidence. These surfaces in the path of the laser beam 201 create excessive astigmatism and coma aberrations that need to be compensated for.

Figure 9A:
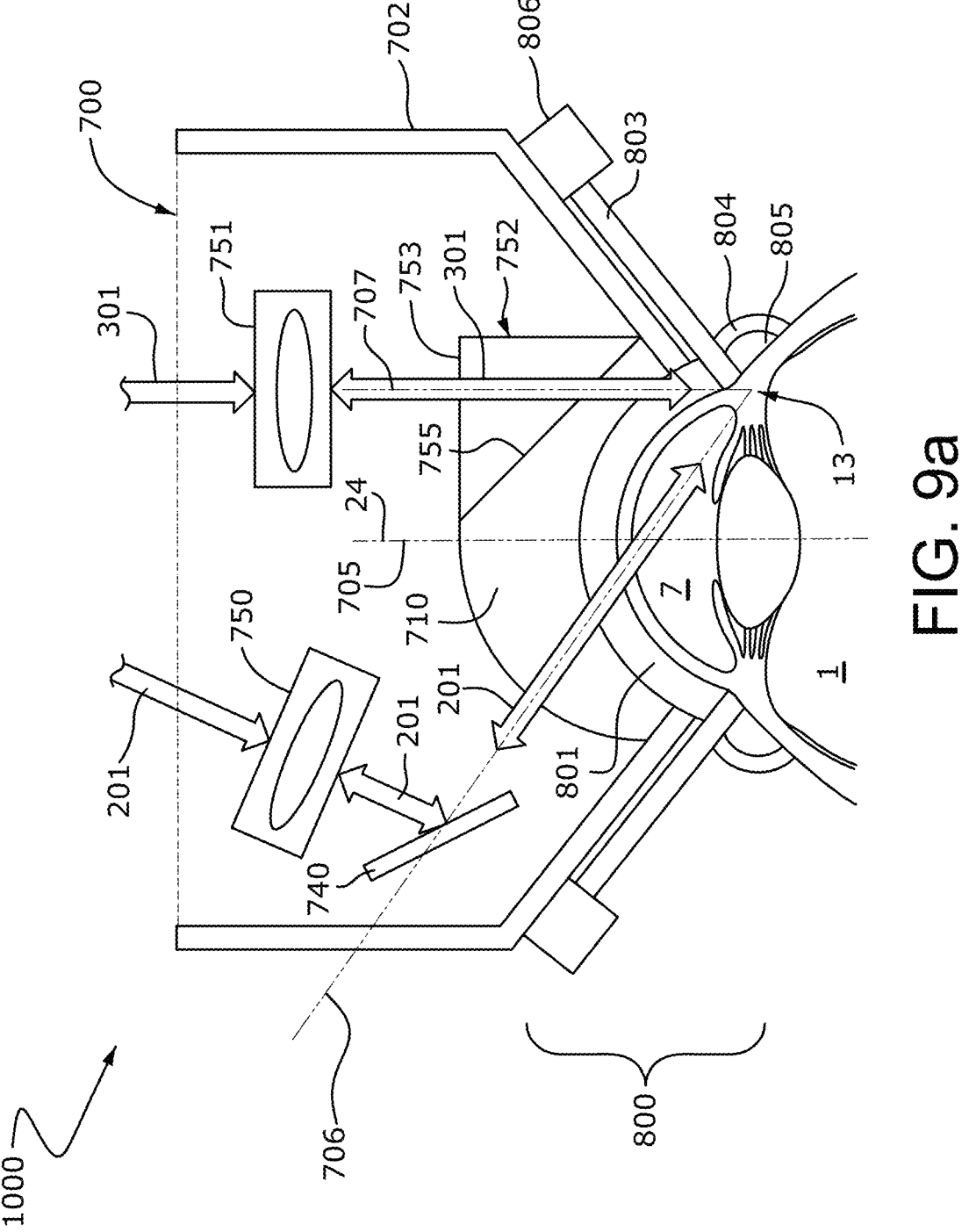
FIG. 9a is a schematic illustration of an embodiment wherein the focusing objective head of the integrated surgical system of FIG. 7 and the patient interface are configured to fixedly coupled together and decouple from each other, and the patient interface is configured to fixedly coupled to and decouple from the eye.
Figure 9B:
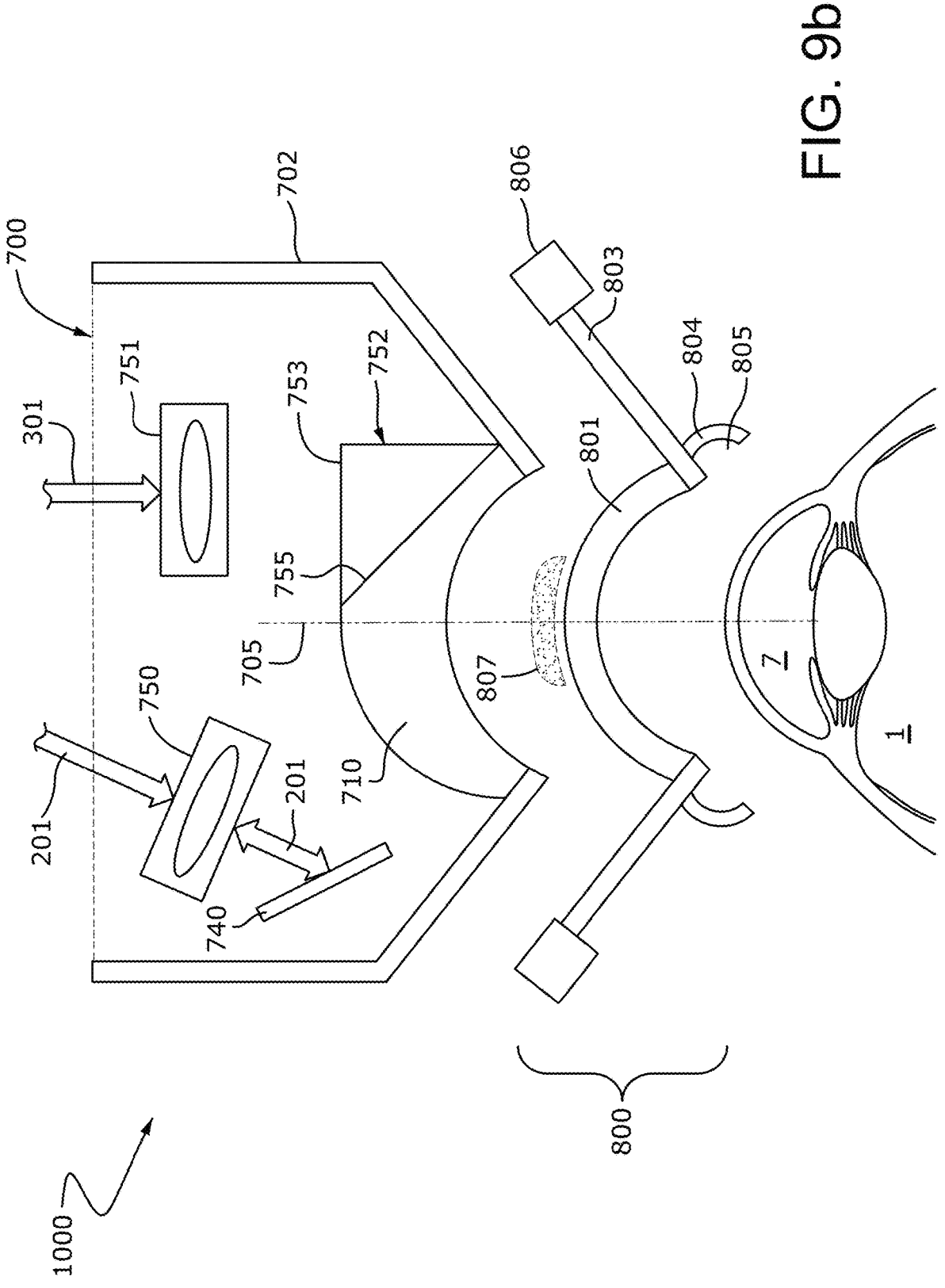
FIG. 9b is schematic illustration of the embodiment of FIG. 9a showing the focusing objective head decoupled from the patient interface and the patient interface decoupled from the eye.

With reference to FIGS. 9a and 9b, in an embodiment of the integrated surgical system 1000 optical components of the focusing objective head 700 and patient interface 800 form a first optical subsystem configured to provide an angled beam path through the cornea and the anterior chamber 7 of the eye 1 into the irido-corneal angle 13 of the eye, and a separate parallel beam path through the cornea and into the irido-corneal angle of the eye while avoiding the anterior chamber and the aqueous humor of the anterior chamber. The parallel beam path is substantially parallel to the first optical subsystem axis 705 of first optical subsystem 1001. The first optical subsystem axis 705 generally aligns with the optical axis 24 of the eye when the first optical subsystem 1001 is coupled to the eye. Thus, the parallel beam path is also substantially parallel to the optical axis 24 of the eye. Substantially parallel means with 20 degrees of parallel.

FIG. 9a shows a condition where both the eye 1, the patient interface 800 and the focusing objective head 700 are coupled together. FIG. 9b shows a condition where the eye 1, the patient interface 800 and the focusing objective head 700 are detached from one another. In each of FIGS. 9a and 9b, for simplicity of illustration the reflecting surface 742 of FIG. 8 is not shown and the path of the OCT beam 301 is shown unfolded.

The patient interface 800 optically and physically couples the eye 1 to the focusing objective head 700, which in turn optically couples with other components of the integrated surgical system 1000. The patient interface 800 serves multiple functions. It immobilizes the eye relative to components of the integrated surgical system; creates a sterile barrier between the components and the patient; and provides optical access between the eye and the components. The patient interface 800 is a sterile, single use disposable device and it is coupled detachably to the eye 1 and to the focusing objective head 700 of the integrated surgical system 1000.

With reference to FIGS. 9a, 9b, 9c, and 13a, the patient interface 800 includes a window 801 that is part of the first optical subsystem 1001. The window 801 has an eye-facing, concave surface 812 and an objective-facing, convex surface 813 opposite the concave surface. The window 801 thus has a meniscus form. The concave surface 812 is characterized by a radius of curvature $r_e$, while the convex surface 813 is characterized by a radius of curvature $r_w$. The concave surface 812 is configured to couple to the eye, either through a direct contact or through index matching material, liquid, or gel 807, placed in between the concave surface 812 and the eye 1. The window 801 may be formed of a solid material and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott AG, Mainz, Germany, allows gamma sterilization of the patient interface 800 without the gamma radiation altering the optical properties of the window 801.

As shown in FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective head 700 to thereby affix the position of the eye relative to the other components of the integrated surgical system 1000. The attachment interface 806 can work with mechanical, vacuum, magnetic or other principles and it is also detachable from the integrated surgical system. In this configuration, the focusing objective head 700 is fixed in place to the patient interface 800, which in turn, is fixed in place to the eye. In other configurations, disclosed later below, an additional component is included between the focusing objective head 700 and the patient interface 800. The additional component is fixed in place relative to the patient interface 800 but not the focusing objective head 700. Instead, the focusing objective head 700 is able to rotate within the additional component without any rotational torque being transferred to the patient interface 800 that is secured to the eye.

Figure 9C:
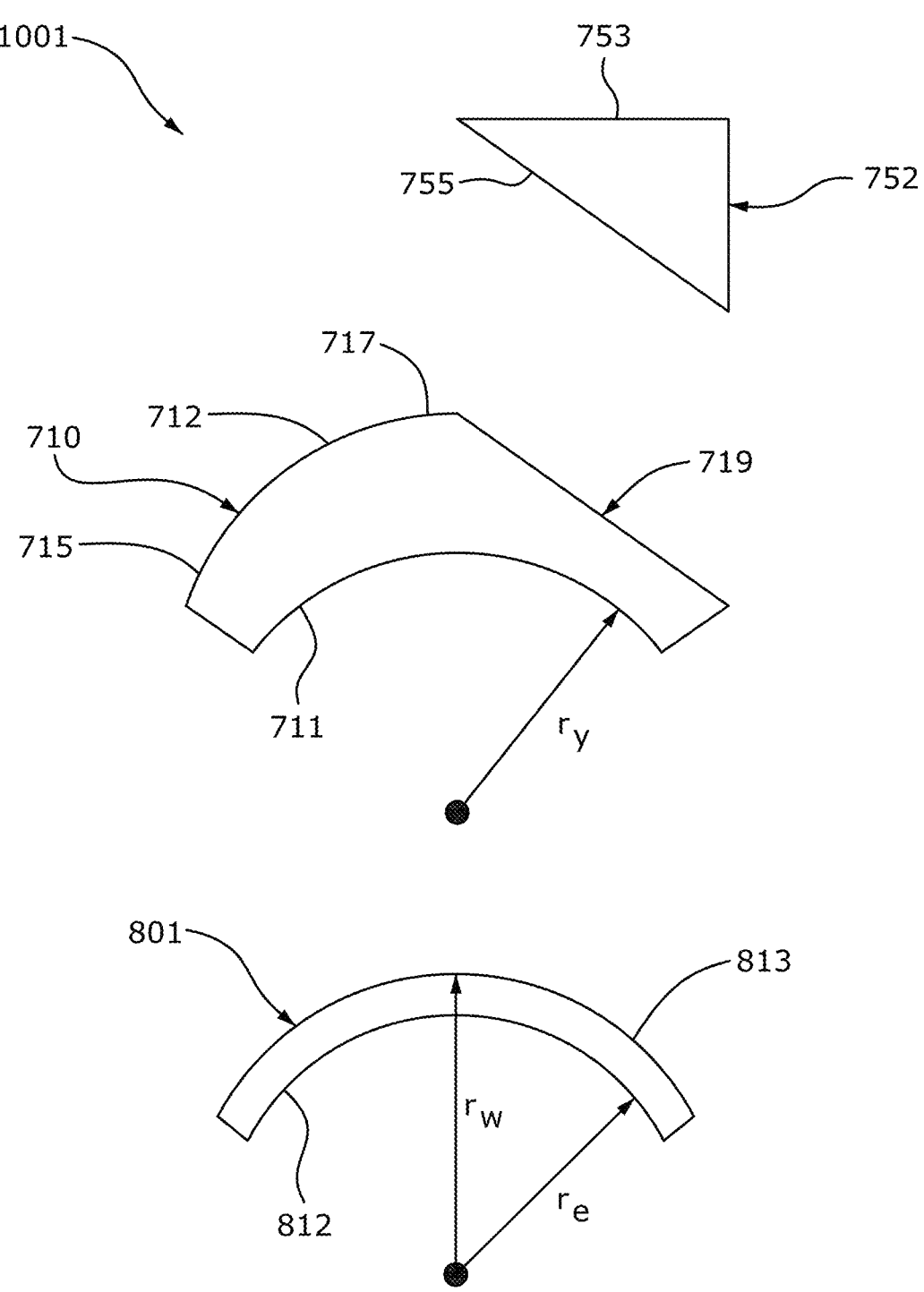
FIG. 9c is an exploded schematic illustration of a configuration of a first optical subsystem formed by optics of the focusing objective head and the patient interface included in FIGS. 9a and 9b.

With reference to FIGS. 9a, 9b, and 9c, the focusing objective head 700 includes an exit lens 710 and a prism 752 that are part of the first optical subsystem 1001. In the configuration shown in these figures, the exit lens 710 is aspheric and includes a concave surface 711 and a generally convex surface 712 opposite the concave surface, and the prism 752 includes an input surface or entry face 753 and an output surface or exit face 755. The generally convex surface 712 of the exit lens 710 includes a modified surface 719 configured to couple to the exit face 755 of the prism 752. In one configuration the modified surface 719 is a flat surface having a geometry that matches the geometry of the exit face 755 of the prism 752. The geometry may be, for example, a rectangle. The exit lens 710 may thus be described as having a generally meniscus form with a modified surface 719. The exit lens 710 and the prism 752 may be formed of a solid material the same as or similar to the window 801 of the patient interface 800. In one embodiment, the exit lens 710 is formed of fused silica and has a refractive index $n_x$ of 1.45. The prism 752 may be formed of fused silica and has a refractive index $n_p$ that is the same as that of the exit lens 710.

With reference to FIG. 9c, the concave surface 711 is characterized by a radius of curvature $r_y$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801.

With reference to FIGS. 10a, 10b, 10c, and 10d alternative configurations of the first optical subsystem 1001 are contemplated, each of which may be used in place of the first optical subsystem of FIGS. 9a-9c. In each of these configurations, optical components of focusing objective head 700 are structured and arranged relative to a window 801 of a patient interface 800 to provide a laser beam path and an OCT beam path functionality similar to that of the configuration of FIGS. 9a-9c. In each of FIGS. 10a, 10b, 10c, and 10d, the exit lens 710a, 710b, 710c, 710d has an extended side region that includes the reflecting surface 740 off which the laser beam 201 reflects to align with the laser axis 706a, 706b, 706c, 706d that extends into the irido-corneal angle of the eye.

Figures 10A, 10B, 10C, 10D:
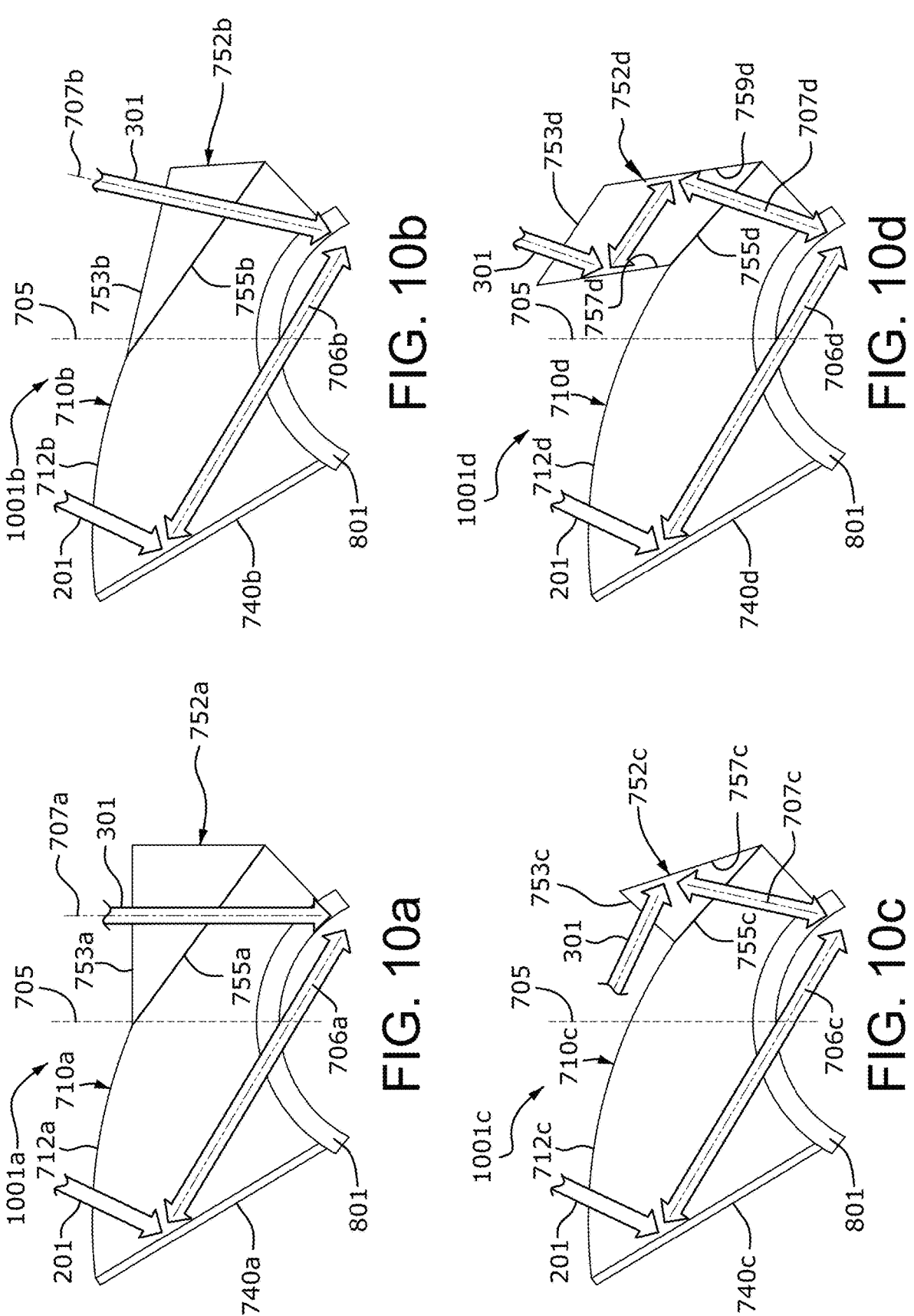
FIGS. 10a, 10b, 10c, and 10d are schematic illustrations of other configurations of first optical subsystems that may be used in place of the first optical subsystem of FIG. 9c.

In FIG. 10a, the prism 752a is similar to the prism of FIG. 9a and directs the OCT beam 301 into the exit lens 710d along an OCT axis 707a that extends into irido-corneal angle of the eye. In FIG. 10b, the prism 752b is configured to direct the OCT beam 301 into the exit lens 710b along an OCT axis 707b that extends into the irido-corneal angle of the eye. In FIGS. 10c and 10d, each of the prisms 752c, 752d has one or more reflecting surface off which the OCT beam 301 reflects into an exit lens 710c, 710d along an OCT axis 707c, 707d that extends into the irido-corneal angle of the eye. In comparing the OCT axes of FIGS. 10a-10d, the OCT axis 707a of FIG. 10a is closer to parallel with the subsystem axis 705 than the OCT axes 707b, 707c, 707d of FIGS. 10b-10d.

Figure 11A:
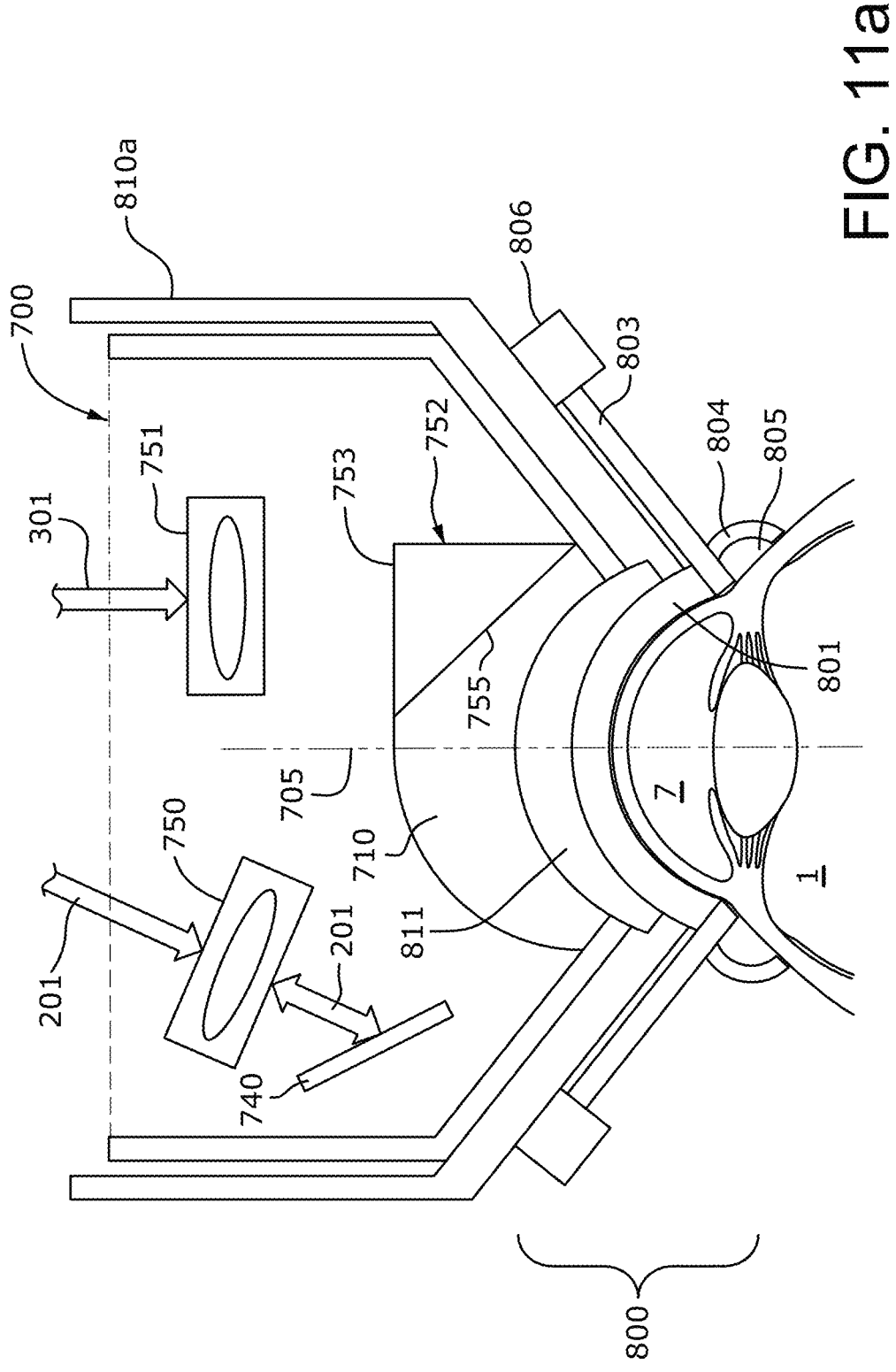
FIG. 11a is a schematic illustration of an embodiment wherein the focusing objective head of the integrated surgical system of FIG. 7 is rotatably coupled to an interface structure that is configured to fixedly coupled to the patient interface and decouple therefrom, and the patient interface is configured to fixedly coupled to and decouple from the eye.
Figure 11B:
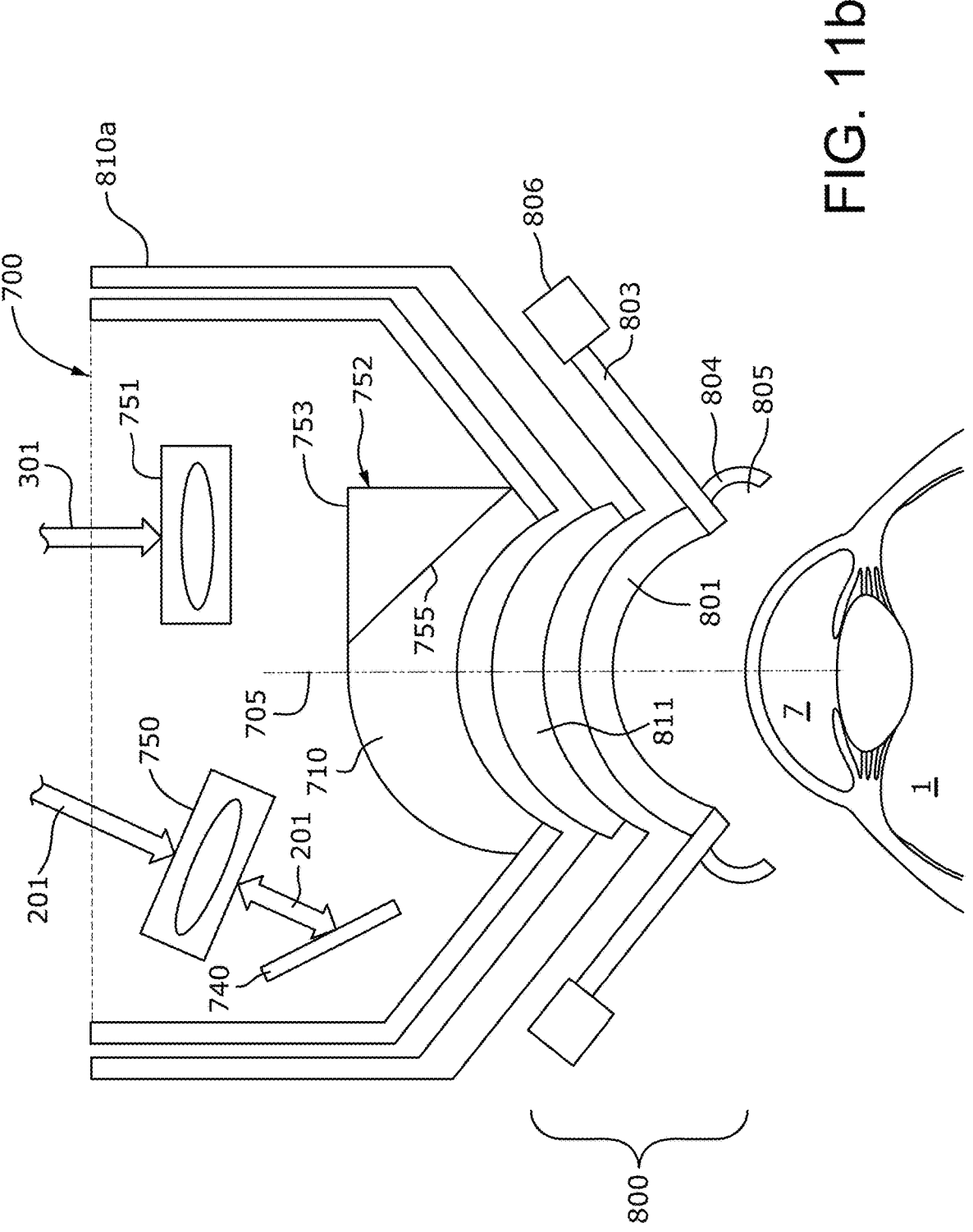
FIG. 11b is a schematic illustration of the embodiment of FIG. 11a showing the focusing objective head decoupled from the interface structure, the interface structure decoupled from the patient interface, and the patient interface decoupled from the eye.

FIGS. 11a and 11b is a schematic illustration of a configuration wherein the focusing objective head 700 is located within an interface structure 810a that couples to the patient interface 800. The focusing objective head 700 and the interface structure 810a are mechanically configured and coupled together to enable rotation of the focusing objective head within the interface structure, relative to the patient interface 800, which is configured to fixedly couple to the eye and decouple therefrom. In this configuration, the focusing objective head 700, including the various optics components 750, 751, 740, 710, 752 shown in FIGS. 11a and 11b, can rotate about the subsystem axis 705 without rotating the patient interface 800. The attachment interface 806 of the patient interface 800 attaches to the non-rotating interface structure 810a. Thus, rotation of the focusing objective head 700 does not translate rotational toque to the patient interface coupled to the eye. In this configuration, the interface structure 810a includes a transparent window 811 through which the laser beam 201 and the OCT beam 301 from the exit lens 710 pass into the window 801 of the patient interface 800.

Figure 12A:
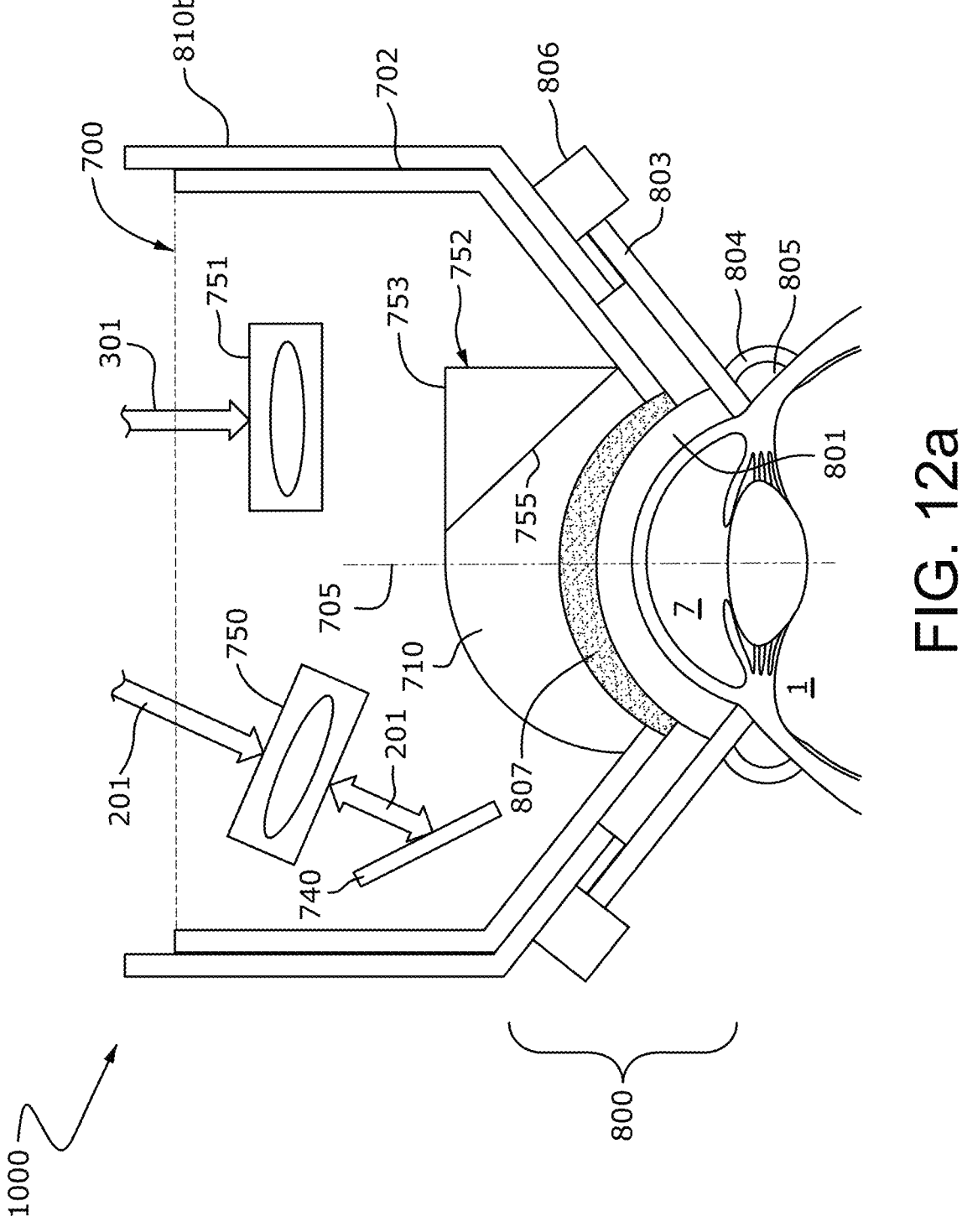
FIG. 12a is a schematic illustration of another embodiment wherein the focusing objective head of the integrated surgical system of FIG. 7 is rotatably coupled to an interface structure that is configured to fixedly coupled to the patient interface and decouple therefrom, and the patient interface is configured to fixedly coupled to and decouple from the eye.
Figure 12B:
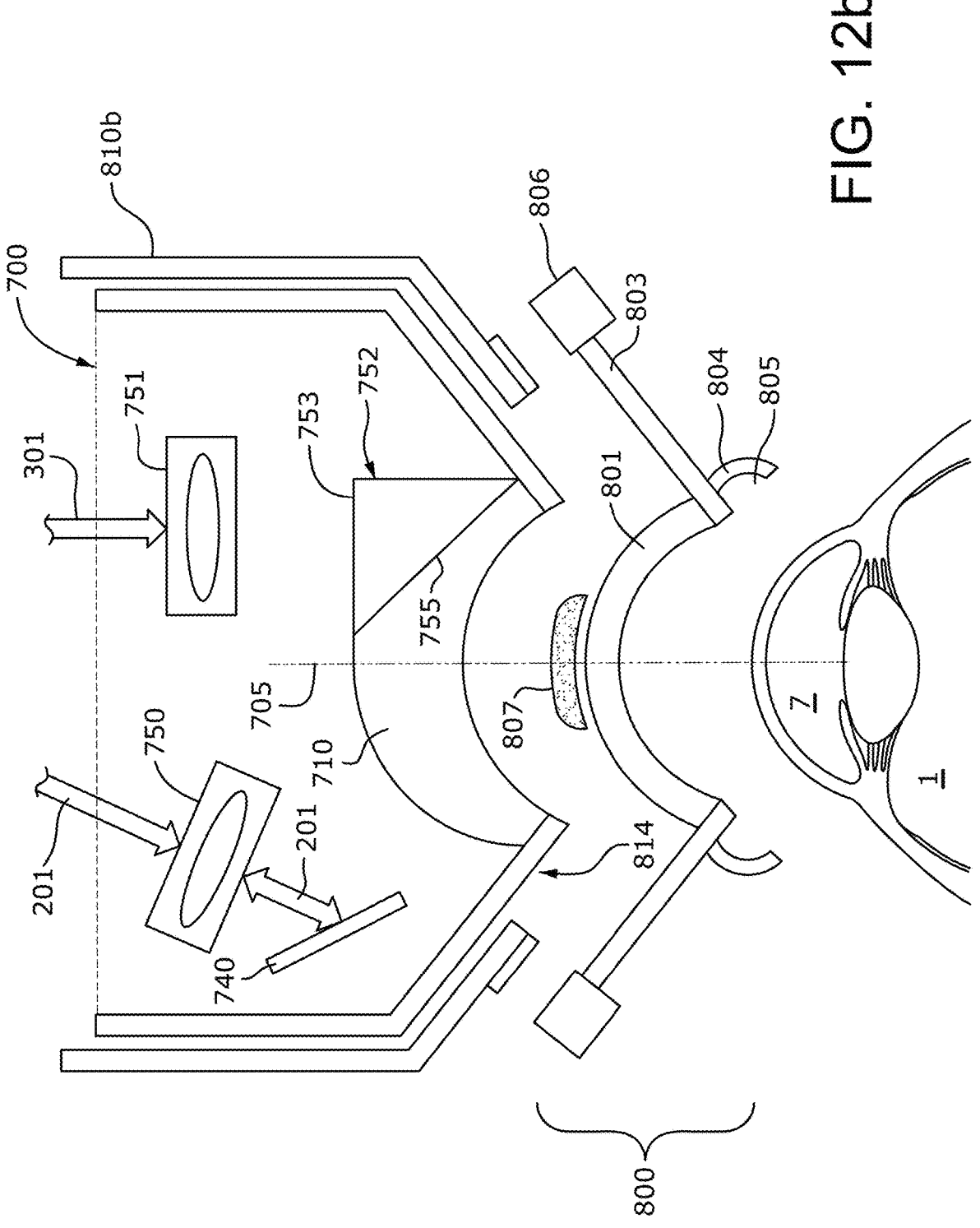
FIG. 12b is a schematic illustration of the embodiment of FIG. 12a showing the focusing objective head decoupled from the interface structure, the interface structure decoupled from the patient interface, and the patient interface decoupled from the eye.

FIGS. 12a and 12b are schematic illustrations of other configurations wherein the focusing objective head 700 is located within an interface structure 810b that couples to the patient interface 800. Like the configuration of FIGS. 11a and 11b, the focusing objective head 700 and the interface structure 810b are mechanically configured and coupled together to enable rotation of the focusing objective head within the interface structure, relative to the patient interface 800, which is configured to fixedly couple to the eye and decouple therefrom. In this configuration, the focusing objective head 700, including the various optics components 750, 751, 740, 710, 752 shown in FIGS. 12a and 12b, can rotate about the subsystem axis 705 without rotating the patient interface 800. The attachment interface 806 of the patient interface 800 attaches to the non-rotating interface structure 810a. Thus, rotation of the focusing objective head 700 does not translate rotational toque to the patient interface coupled to the eye. In this configuration, the interface structure 810b includes an opening 814 through which laser beams 201 and OCT beams 301 from the exit lens 710 pass into the window 801. An index matching material, liquid, or gel 807 is placed on the convex surface of the window 801 to create a layer between the exit lens 710 and the window upon coupling of the components 800, 810b, 700.

Figure 13B:
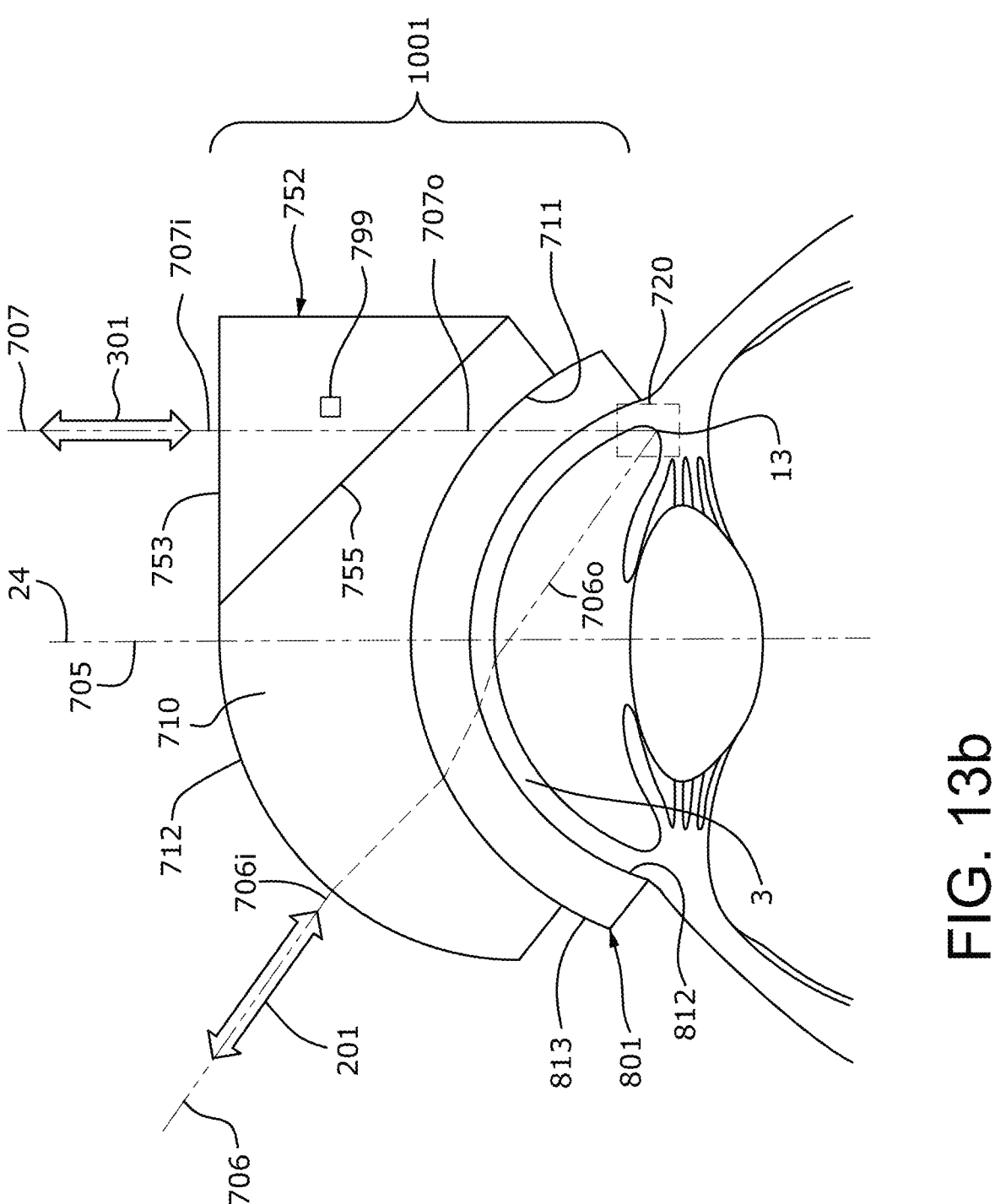
FIG. 13b is a schematic illustration of a laser beam passing through the first optical subsystem of FIG. 13a along an angled beam path into the eye, and an OCT beam passing through the first optical subsystem along a parallel beam path.

FIG. 13a is a schematic illustration of components of the integrated surgical system 1000 of FIGS. 7 and 8 functionally arranged to form an optical system 1010 having a first optical subsystem 1001 and a second optical subsystem 1002 that enable multi-path access to a common surgical volume 720 in the irido-corneal angle 13, including access by a laser beam 201 along an angled beam path to the surgical volume, and access by an OCT beam 301 along a parallel beam path to the surgical volume. FIG. 13b is a schematic illustration of a laser beam 201 and an OCT beam 301 passing through the first optical subsystem of FIG. 13a.

The optical system 1010 shown in FIG. 13a includes components of the focusing objective head 700 and the patient interface 800 of FIG. 9a. However, for simplicity, all components of the focusing objective head 700 and the patient interface 800 are not included in FIG. 13a and reflections of the laser beam 201 and the OCT beam 301 are not shown. For example, with respect to the laser beam 201, the reflecting surface 740 of the focusing objective head 700 shown in FIGS. 8 and 9a is not shown in FIG. 13a, and the path of the laser beam is shown unfolded or straightened out and directly incident on the exit lens 710 of the focusing objective head 700. With respect to the OCT beam 301, the reflecting surface 742 of the focusing objective head 700 shown in FIG. 8 is not shown in FIG. 13a and the path of the OCT beam is shown unfolded and directly incident on the prism 752 like shown in FIG. 9a.

It is understood by those skilled in the art that adding or removing planar beam folding mirrors or other types of reflecting surfaces does not alter the principal working of the optical system 1010 formed by the first optical subsystem 1001 and the second optical subsystem 1002. It is also understood that the configuration of optics components, e.g., the exit lens 710 and the prism 752 of the focusing objective head 700, are schematic in nature and that numerous other configurations are contemplated as previously described with reference to FIGS. 10a, 10b, 10c, and 10d.

With reference to FIG. 13a, a first optical subsystem 1001 of the integrated surgical system 1000 includes the prism 752 and the exit lens 710 of a focusing objective head 700 and the window 801 of a patient interface 800. The prism 752, exit lens 710, and window 801 are arranged relative to each other to define a first optical subsystem axis 705. The first optical subsystem 1001 is configured to receive a laser beam 201, incident at the convex surface 712 of the exit lens 710 along a second optical axis or laser axis 706, and to direct the laser beam through the cornea and the anterior chamber of the eye and into a surgical volume 720 in the irido-corneal angle 13 of the eye. The first optical subsystem 1001 is also configured to receive an OCT beam 301, incident at the entry face 753 of the prism 752 along a third optical axis or OCT axis 707, and to direct the OCT beam through the cornea of the eye and into the surgical volume 720 in the irido-corneal angle 13 of the eye without passing through the anterior chamber and the aqueous humor of the anterior chamber.

During a surgical procedure, the first optical subsystem 1001 may be assembled by interfacing the convex surface 813 of the window 801 with the concave surface 711 of the exit lens 710. To this end, a focusing objective head 700 is docked together with a patient interface 800. As a result, the concave surface 711 of the exit lens 710 is coupled to the convex surface 813 of the window 801. With reference to FIG. 9b, the coupling may be by direct contact between the exit lens 710 and the window 801 or by indirect contact through a layer of index matching fluid. For example, when docking the patient interface 800 to focusing objective head 700, a drop of index matching fluid or gel 807 can be applied between the contacting surfaces to eliminate any air gap that may be between the two surfaces 711, 813 to thereby help pass each of the laser beam 201 and the OCT beam 301 through the gap with minimal Fresnel reflection and distortion. With reference to FIG. 11a, the coupling between the exit lens 710 and the window 801 may be by indirect contact through a transparent window 811 of an interface structure 810a. With reference to FIG. 12a, the coupling between the exit lens 710 and the window 801 may be by indirect contact through a layer of index matching fluid or gel 807 within the opening 814 of an interface structure 810b.

In order to direct the laser beam 201 through the cornea and the anterior chamber of the eye and into the surgical volume 720 in the irido-corneal angle 13 of the eye, the first optical subsystem 1001 is designed to account for refraction of the laser beam as it passes through the exit lens 710, the window 801 and the cornea 3. To this end, and with reference to FIG. 13b, the refractive index $n_x$ of the exit lens 710 and the refractive index $n_w$ of the window 801 are selected in view of the refractive index $n_c$ of the cornea 3 to cause appropriate beam bending through the first optical subsystem 1001 so that when the beam 701 exits the subsystem and passes through the cornea 3, the beam path is generally aligned to fall within the irido-corneal angle 13.

Continuing with reference to FIG. 13b and beginning with the interface between the window 801 and the cornea 3. Too steep of an angle of incidence at the interface where the laser beam 201 exits the window 801 and enters the cornea 3, i.e., at the interface between the concave surface 812 of the window and the convex surface of the cornea 3, can create excessive refraction and distortion. To minimize refraction and distortion at this interface, in one embodiment of the first optical subsystem 1001, the refractive index of the window 801 is closely matched to the index of the cornea 3.

Excessive refraction and distortion at the interface where the laser beam 201 exits the window 801 and enters the cornea 3 may be further compensated for by controlling the bending of the beam 701 as it passed through the exit lens 710 and the window 801. To this end, in one embodiment of the first optical subsystem 1001 the index of refraction $n_w$ of the window 801 is larger than each of the index of refraction $n_x$ of the exit lens 710 and the index of refraction $n_c$ of the cornea 3. As a result, at the interface where the laser beam 201 exits the exit lens 710 and enters the window 801, i.e., interface between the concave surface 711 of the exit lens and the convex surface 813 of the window, the beam passes through a refractive index change from high to low that cause the beam to bend in a first direction. Then, at the interface where the laser beam 201 exits the window 801 and enters the cornea 3, i.e., interface between the concave surface 812 of the exit lens and the convex surface of the cornea, the beam passes through a refractive index change from low to high that cause the beam to bend in a second direction opposite the first direction.

The shape of the window 801 is chosen to be a meniscus lens. As such, the incidence angle of light has similar values on both surfaces 812, 813 of the window 801. The overall effect is that at the convex surface 813 the light bends away from the surface normal and at the concave surface 812 the light bends towards the surface normal. The effect is like when light passes through a plan parallel plate. Refraction on one surface of the plate is compensated by refraction on the other surface a light passing through the plate does not change its direction. Refraction at the entering, convex surface 712 of the exit lens 710 distal to the eye is minimized by setting the curvature of the entering surface such that the angle of incidence β of the laser beam 201 at the entering surface is close to a surface 709 that is normal to the entering surface 712 at the intersection point 708.

In order to direct the OCT beam 301 through the cornea and into the surgical volume 720 in the irido-corneal angle 13 of the eye while avoiding the anterior chamber, the prism 752 of the first optical subsystem 1001 is arranged and designed to receive the OCT beam 301 traveling along an input axis 707i through the entry face 753, and to direct the OCT beam 301 along an output axis 707o parallel to, or close to parallel, to the optical axis 24 of the eye such that the OCT beam is focused at the surgical volume 720, e.g., the trabecular meshwork. The angle of incidence of the OCT beam 301 on the entry face 753 is in the range of 0-10 degrees.

In the configuration of FIGS. 13a and 13b, the prism 752 of the first optical subsystem 1001 includes two surfaces: 1) an entry face 753 and an exit face 755. Similar prisms 752a, 752b are shown in FIGS. 10a and 10b. In other configurations, such as shown FIGS. 10c and 10d, the prism 752c, 752d of the first optical subsystem 1001 has more than two surfaces, including: 1) an entry face 753c, 753d, 2) one or more reflective facets 757c, 757d, 759d, and 3) an exit face 755c, 755d. These configurations of prisms 752c, 752d are solutions that address two challenges: 1) the very tight space constraints within the focusing objective head 700, and 2) ensuring the OCT beam 301 reaches the surgical volume 720. In the prism 752c of FIG. 10c, any permutation of the subtended angles between the three surfaces 753c, 757c, 755c and the refractive index of the prism material that results in the output light axis being close to parallel to the optical axis of the eye is possible. Likewise, in the prism 752d of FIG. 10d, any permutation of the subtended angles between the four surfaces 753d, 757d, 759d, 755d and the refractive index of the prism material that results in the output light axis being close to parallel to the optical axis of the eye is possible.

The location of the prism centroid 799 relative to the optical axis 24 of the eye also contributes to the focus location. If the prism 752 is decentered along an axis perpendicular to the optical axis 24, then this will correspond to the focal point on the image plane also being decentered along the same perpendicular axis. The exit lens 710 is altered to ensure accurate spatial placement of the prism 752 to within an acceptable level of decentration. The alteration can consist of any machined features, such as the flat modified surface 719 described above reference to FIG. 9c that the prism 752 can be registered against during the process of adhering the prism to the exit lens 710. The permanent, physical mating of the prism 752 to the exit lens 710 is accomplished using an index-matched, optical grade epoxy.

To prevent aberrations, generally, the angle of incidence between the prism entry face 753 and the input axis 707i is between 0-10 degrees. The prism 752 is bonded to the exit lens 710 and precisely located in space by machining features into the exit lens such that the exit face 755 mates to the modified surface 719 of the exit lens 710.

Figures 1, 2, 3, 10E:
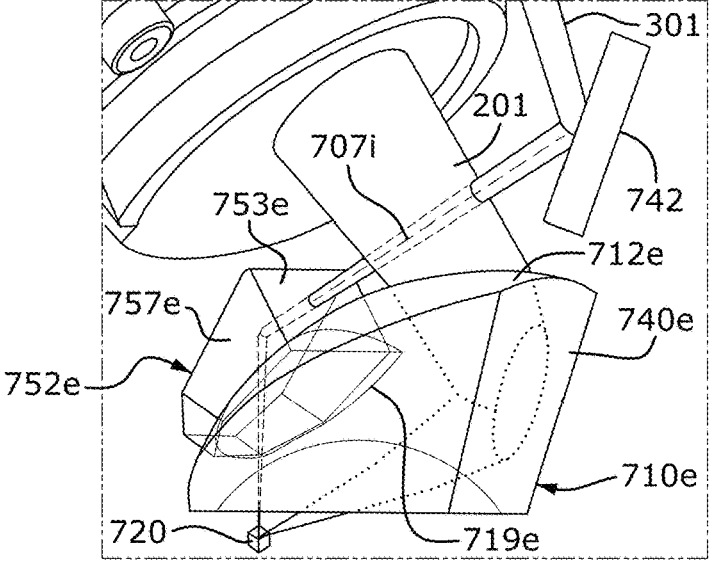

With reference to FIG. 10e due to the curved top surface 712e of the exit lens 710e, without the prism 752e, the angle of incidence of the input OCT beam along the OCT input axis 707i would be high and the refraction angle steep. Considering the extremely limited space within the focusing objective head 700, it may be geometrically difficult to direct the OCT beam 301 at an angle relative to curved top surface 712e of the exit lens 710e such that the OCT beam would strike the surgical volume 720. To address this, the prism 752e of FIG. 10e has three faces: an entry face 753e, a reflective surface 757e and an exit face 755e. The prism 752e is designed and mechanically positioned so that the nominal OCT beam 301 angle of incidence on the entry face 753e is normal, and the OCT beam scanner has minor deviation (+/−10 degrees), which minimizes the scanned beams refraction and therefore aberrations. There are several other design measures implemented to reduce the refractive angle change. Firstly, the prism 752e is made from the same material as the exit lens 710e. Secondly, a region of the top surface 712e is modified to have an angled flat face machined for prism placement and registration to bond the prism to the exit lens 710e. The modified surface 719e includes an angled flat face that is parallel to the exit face 755e of the prism 752e. As the exit face 755e of the prism 752e and modified surface 719e are parallel and the prism and exit lens 710e are of the same material, there is no refraction when the OCT beam 301 traverses the prism-lens interface.

With reference to FIG. 13a, the first optical subsystem 1001 comprises a subsystem axis 705 that substantially aligns with the optical axis 24 of the eye when the focusing objective head 700 and the patient interface 800 are coupled to the eye. When coupled to the eye 1, the OCT output axis 707o is parallel or near parallel with the subsystem axis 705 and is radially offset from the subsystem axis 705 (and thus the optical axis 24) by a distance such that the OCT beam 301 avoids the anterior chamber 7 of the eye.

With continued reference to FIG. 13a, the first optical subsystem 1001 has a first region 754 having an entry face 753 and a second region 756 having an entry surface 712 that are spaced apart relative to the subsystem axis 705. In FIG. 13a, the first region 754 and the second region 756 are illustrated as being on opposite sides of the subsystem axis 705. The entry face 753 may be flat, while the entry surface 712 may be curved. With continued reference to FIG. 13*a*, the second optical subsystem 1002 is optically coupled to the first optical subsystem 1001 such that the laser beam 201 provided by the second optical subsystem 1002 travels along a laser input axis 706*i* incident at a point associated with the entry surface 712. The second optical subsystem 1002 is also optically coupled to the first optical subsystem 1001 such that the OCT beam 301 provided by the second optical subsystem 1002 travels along an OCT input axis 707*i* incident at a point associated with the entry face 753.

The second optical subsystem 1002 includes various components including components of the beam conditioners between the subsystem axis 705 and the laser axis 706, and the angle δ between the laser axis 706 and the OCT axis 707, and the offset between the first optical subsystem axis 705 and the OCT axis 707.

With considerations described above with reference to FIGS. 9*a*, 9*b* and 9*c*, the design of the first optical subsystem 1001 is optimized for angled optical access at an angle α relative to the first optical subsystem axis 705 of the first optical subsystem 1001. Optical access at the angle α compensates for optical aberrations of the first optical subsystem 1001. Table 1 shows the result of the optimization at access angle α=72 degrees with Zemax optical design software package. This design is a practical embodiment for image guided femtosecond glaucoma surgery.

TABLE 1

| Surface | Structure | Material | Refractive index | Radius [mm] | Center Thickness [mm] |
|---|---|---|---|---|---|
| input surface or entry face 753; output surface or exit face 755 | prism 752 of focusing objective head 700 | fused silica | 1.45 | infinity | 4.0 |
| concave surface 711, convex surface 712 (including modified surface 719) | exit lens 710 of focusing objective head 700 | fused silica | 1.45 | −10 | 4.5 |
| concave surface 812, convex surface 813 | window 801 of patient interface 800 | BK7G18 | 1.50 | −10.9 | 1.0 |
| | cornea 3 | corneal tissue | 1.36 | −7.83 | 0.54 |
| | aqueous humor 8 | aqueous humor | 1.32 | −6.53 | 3.5 |
| target volume 720 | trabecular meshwork 12 | ophthalmic tissue | 1.38 | N/A | 0 to 1 mm | and scanners 500, such as the beam conditioner 510 and transverse scanning mirrors 530, 532 associated with the laser source 200 as shown in FIG. 8, and the beam conditioner 511 and scanning mirrors 531, 533 associated with the OCT imaging apparatus 300. The second optical subsystem 1002 also includes the laser focusing lens 750 and the OCT focusing lens 751 shown in FIG. 8.

With additional reference to FIGS. 9*b*, 11*b*, and 12*b*, some components of the first optical subsystem 1001 and the second optical subsystem 1002 are mechanically associated with the focusing objective head 700. These components include, for example, the exit lens 710 of the first optical subsystem 1001 and the laser focusing lens 750 and the OCT focusing lens 751 of the second optical subsystem 1002. As previously described, in the embodiments of FIGS. 11*b* and 12*b*, the focusing objective head 700 is configured to rotate relative to a fixed patient interface 800. With additional reference to FIG. 13*a*, rotating the focusing objective head 700 as such, the laser beam 201 provided by the second optical subsystem 1002 and the laser axis 706 through the first optical subsystem 1001 rotate together relative to the fixed window 801 and around the subsystem axis 705. Similarly, the OCT beam 301 provided by the second optical subsystem 1002 and the OCT axis 707 through the first optical subsystem 1001 rotate together relative to the fixed window 801 and around the subsystem axis 705. This allows optical access to the whole 360-degree circumference of the irido-corneal angle 13 of the eye 1 by each of the laser beam 201 and the OCT beam 301 while preserving the angle α

This design produces diffraction limited focusing of 1030 nm wavelength laser beams and 850 nm wavelength OCT beams with numerical aperture (NA) up to 0.2. In one design, the optical aberrations of the first optical subsystem are compensated to a degree that the Strehl ratio of the first optical subsystem for a beam with numerical aperture larger than 0.15 at the irido-corneal angle is larger than 0.9. In another design, the optical aberrations of the first optical subsystem are partially compensated, the remaining uncompensated aberrations of the first optical system are compensated by the second optical subsystem to a degree that the Strehl ratio of the combined first and second optical subsystem for a beam with numerical aperture larger than 0.15 at the irido-corneal angle is larger than 0.9.

With reference to FIGS. 8-13*b*, disclosed is a focusing objective head 700 configured to couple to a patient interface 800. The patient interface 800 includes a window 801 that is configured to couple to a cornea of an eye 1. The focusing objective head 700 includes an exit lens 710 and a prism 752 that is mechanically and optically coupled to the exit lens. The exit lens 710 and prism 752 collectively form an optical assembly that is mechanically secured to a housing 702 of the focusing objective head 700. The exit lens 710 is configured to optically couple to the window 801 of the patient interface 800 to align an axis 705 of the exit lens with an optical axis 24 of the eye 1. With reference to FIG. 13*a*, the optical assembly formed by the exit lens 710 and the prism 752 is configured to receive an OCT beam 301 along an OCT input axis 707*i* incident to an entry face 753 of the prism, and to direct the OCT beam to an OCT output axis 707*o*. The OCT output axis 707*o* is substantially parallel to the axis 705 of the exit lens 710, is radially offset from the axis of the exit lens, and extends through the exit lens into the cornea and into the irido-corneal angle 13 of the eye 1. The optical assembly formed by the exit lens 710 and the prism 752 is also configured to receive a laser beam 201 along a laser input axis 706*i* incident to an entry surface 712 of the exit lens 710, and to direct the laser beam along an angled optical path 706 (also referred to herein as a "laser optical path" or a "laser axis") through the exit lens, through the cornea, through the anterior chamber 7, and into a target volume 720 of ocular tissue in the irido-corneal angle 13. To this end, the optical assembly formed by the exit lens 710 and the prism 752 includes a reflecting surface 740 arranged to direct the laser beam 201 along the angled optical path 706.

With reference to FIGS. 9*a* and 9*b*, in some embodiments the housing 702 of the focusing objective head 700 is configured to directly couple to the patient interface 800. With reference to FIGS. 11*a*, 11*b*, 12*a*, and 12*b*, in some embodiments the housing 702 of the focusing objective head 700 is configured to indirectly couple to the patient interface 800 through an interface structure 810*a*, 810*b* that is configured to mechanically couple between the housing and the patient interface. In these embodiments, the housing 702 of the focusing objective head 700 is configured to rotate within the interface structure 810*a*, 810*b* to thereby rotate the optical assembly formed by the exit lens 710 and the prism 752 about the axis 705 of the exit lens and the optical axis 24 of the eye 1 while the patient interface 800 and its window 810 remain fixed in place relative to the eye.

With reference to FIGS. 8, 10*e*, and 13*a*, the focusing objective head 700 may include an OCT mirror 742 secured to the housing 702 and arranged relative to the optical assembly formed by the exit lens 710 and the prism 752 to direct the OCT beam 301 along the OCT input axis 707*i* incident to the entry face 753 of the prism 752. The focusing objective head 700 may further include an OCT focusing lens 751 (shown in FIGS. 8 and 13*a*) that is mechanically secured to the housing 702 and arranged relative to the OCT mirror 742 (shown in FIG. 8) to receive the OCT beam 301 from an OCT imagining apparatus 300 and to direct the OCT beam to the OCT mirror. The focusing objective head 700 may further include a laser focusing lens 750 that is mechanically secured to the housing 702 and arranged relative to the optical assembly formed by the exit lens 710 and the prism 752 to receive the laser beam 201 and to direct the laser beam to the entry surface 712 of the exit lens. The focusing objective head 700 may also include a laser scanner 500 (shown in FIG. 13*a*) secured to the housing 702 and arranged and optically coupled between the laser source 200 and the laser focusing lens 750.

While details of the mechanical coupling of the laser focusing lens 750, the OCT focusing lens 751, the OCT mirror 742, and the laser scanner 500 to the housing 702 are not illustrated, various means or mechanisms may be used to secure these components to the interior of the housing at appropriate locations relative to the optical assembly formed by the exit lens 710 and the prism 752.

Minimally Invasive Surgical Treatments

Figure 14:
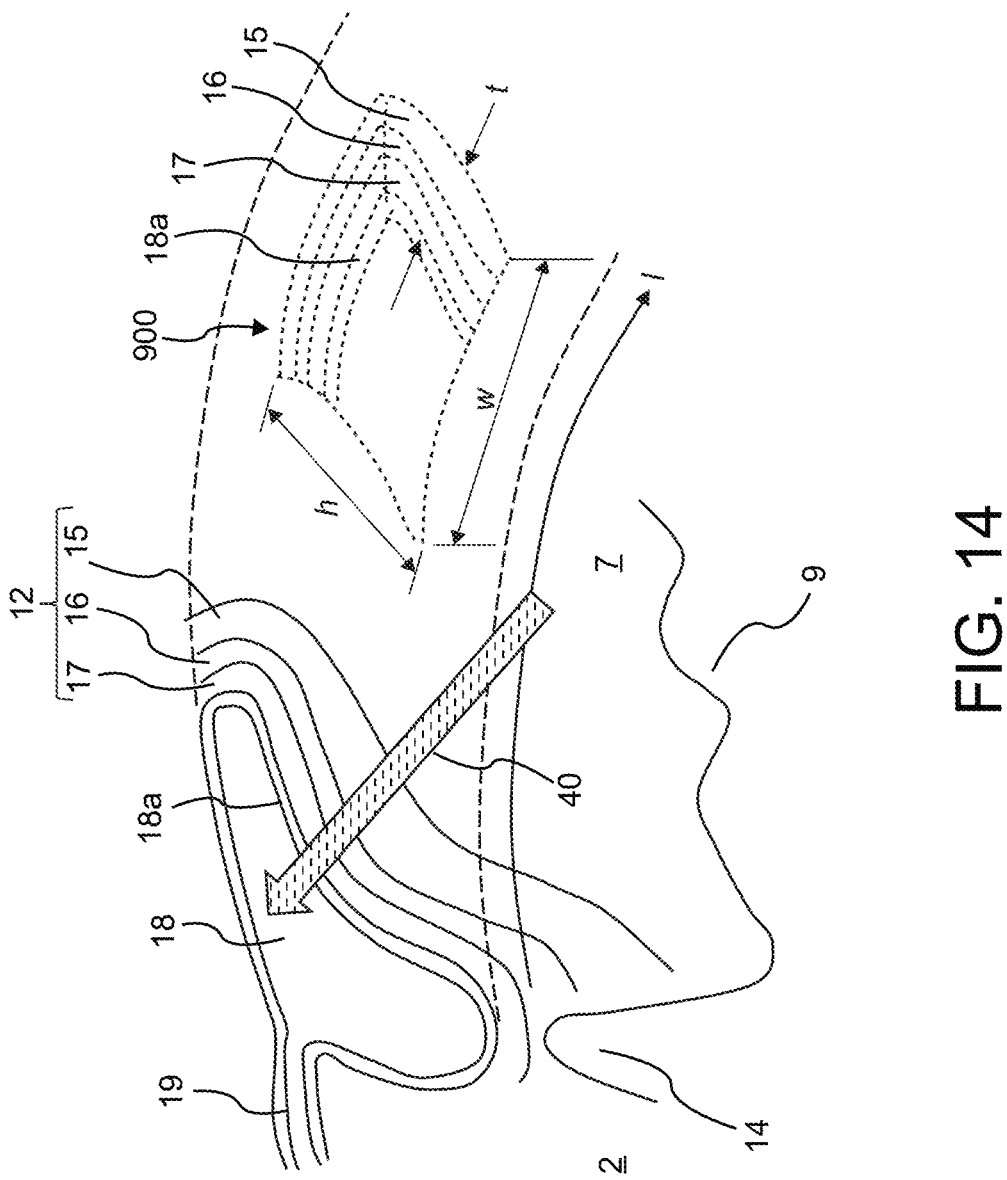
FIG. 14 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by the integrated surgical system of FIG. 7.

FIG. 14 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal 15, the corneoscleral meshwork 16, and the juxtacanalicular tissue 17. These layers are porous and permeable to aqueous, with the uveal 15 being the most porous and permeable, followed by the corneoscleral meshwork 16. The least porous and least permeable layer of the trabecular meshwork 12 is the juxtacanalicular tissue 17. The inner wall 18*a* of the Schlemm's canal 18, which is also porous and permeable to aqueous, has characteristics similar to the juxtacanalicular tissue 17.

Figure 15:
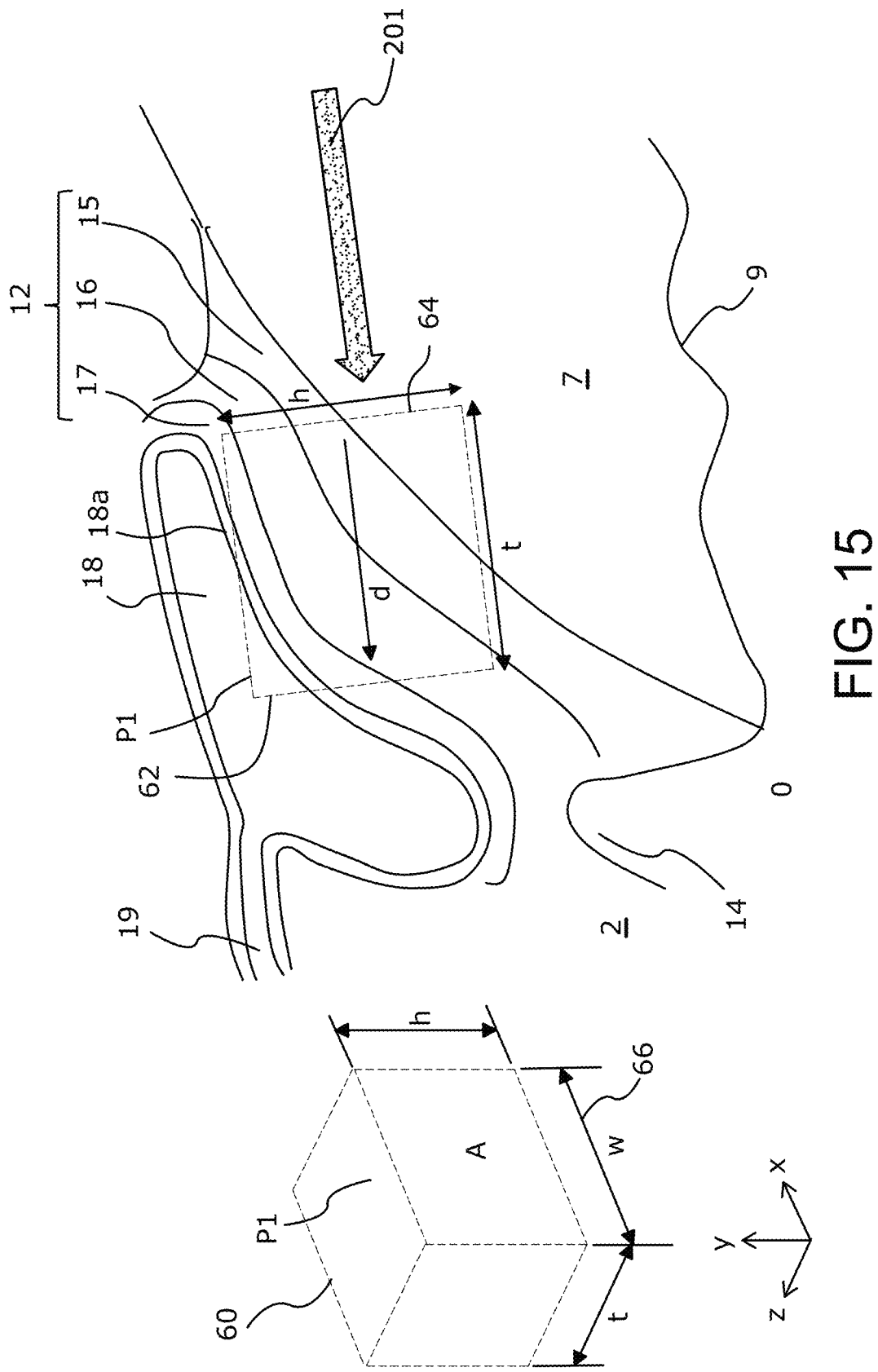
FIG. 15 is a two-dimensional schematic illustrations of anatomical structures in the irido-corneal angle and a three-dimensional laser treatment pattern to be applied by the integrated surgical system of FIG. 7 to affect a surgical volume of ocular tissue between the Schlemm's canal and the anterior chamber as shown in FIG. 14.
Figure 16:
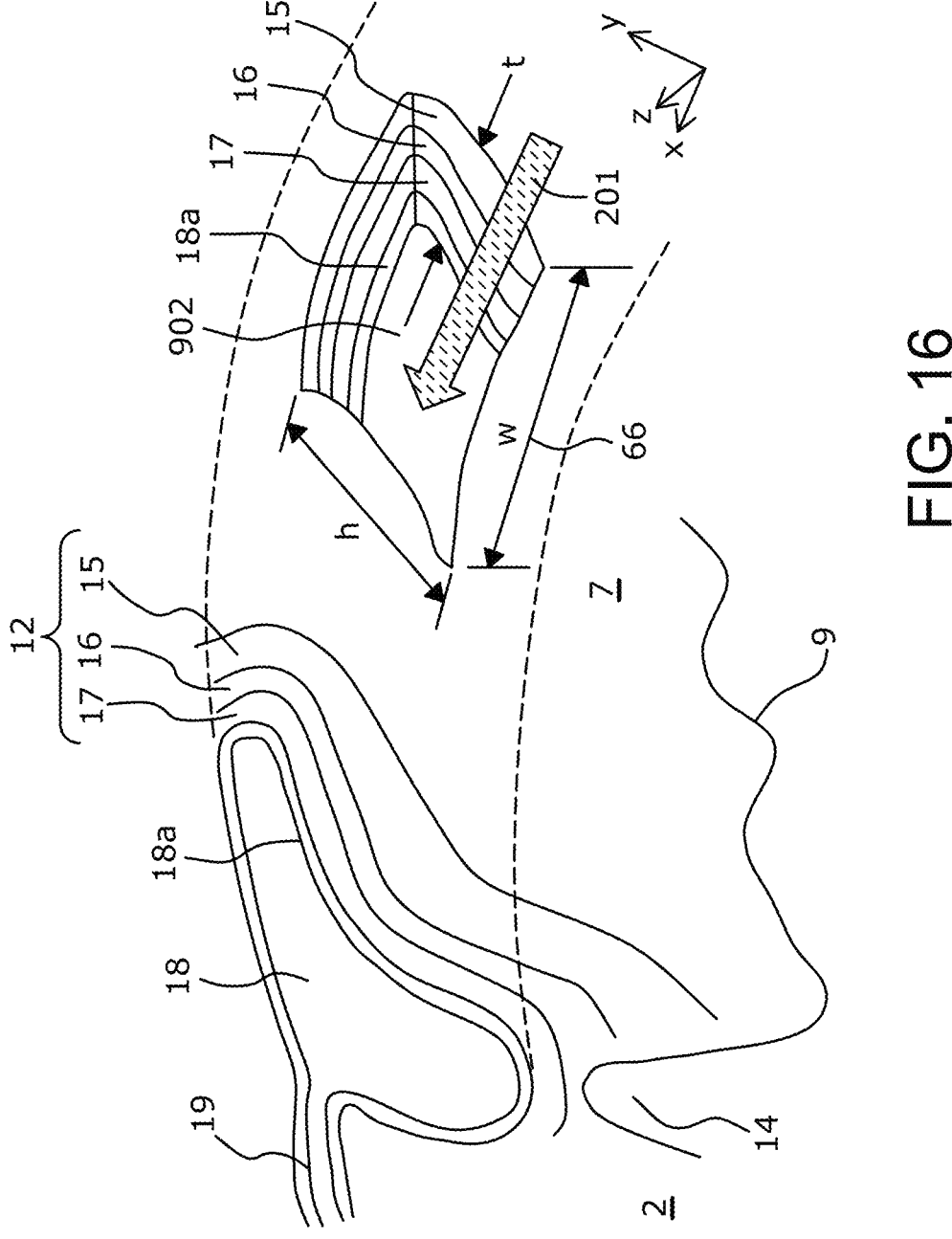
FIG. 16 is a three-dimensional schematic illustration of FIG. 14 subsequent to treatment of the surgical volume of ocular tissue by a laser based on the laser treatment pattern of FIG. 15 that forms an opening between the Schlemm's canal and the anterior chamber.

FIG. 15 includes three-dimensional illustrations of a treatment pattern P1 to be applied by the integrated surgical system 1000 to affect the surgical volume 900 of ocular tissue shown in FIG. 14, and a two-dimensional schematic illustration of the treatment pattern P1 overlaying anatomical structures to be treated. FIG. 16 is a three-dimensional schematic illustration of the anatomical structures of the eye including an opening 902 through the trabecular meshwork 12 that results from the application of the laser treatment pattern of FIG. 15. The opening 902 may also be referred to as a channel or aperture. The opening 902 provides and outflow pathway 40 that reduces the flow resistance in the ocular tissue to increase aqueous flow from the anterior chamber 7 into the Schlemm's canal 18 and thereby reduce the IOP of the eye.

Surgical treatments reduce outflow pathway resistance while minimizing ocular tissue modification through design and selection of laser treatment patterns. A treatment pattern is considered to define a collection of a laser-tissue interaction volumes, referred to herein as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. The arrangement of the cells may resemble the arrangement of atoms in a crystal structure.

With reference to FIG. 15, a treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the lateral extent of the treatment, w. A treatment thickness t that represents the level to which the laser will cut into the ocular tissue from the distal extent or border of the treatment volume at or near Schlemm's canal 18 to the proximal extent or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model.

Additional surgical parameters define the placement of the surgical volume or affected volume within the eye. For example, with reference to FIGS. 14 and 15, placement parameters may include one or more of a location l that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

With reference to FIGS. 14 and 15, a surgical volume 900 of ocular tissue to be treated is identified by the integrated surgical system 1000 and a treatment pattern P1 corresponding to the surgical volume is designed by the integrated surgical system. Alternatively, the treatment pattern P1 may be designed first, and then an appropriate surgical volume 900 for applying the treatment pattern may be identified. The surgical volume 900 of ocular tissue may comprise portions of the trabecular meshwork 12 and the Schlemm's canal 18. For example, the surgical volume 900 of ocular tissue shown in FIG. 14 includes portions of the uveal 15, the corneoscleral meshwork 16, the juxtacanalicular tissue 17, and the inner wall 18a of the Schlemm's canal 18. The treatment pattern P1 defines a laser scanning procedure whereby a laser is focused at different depth locations in ocular tissue and then scanned in multiple directions to affect a three-dimensional volume of tissue comprising multiple sheets or layers of affected tissue.

With reference to FIGS. 15 and 16, during a laser scanning procedure, a surgical laser beam 701 may scan ocular tissue in accordance with the treatment pattern P1 to form an opening 902 that extends from the anterior chamber 7, through each of the uveal 15, the corneoscleral meshwork 16, the juxtacanalicular tissue 17 of the trabecular meshwork 12, and the inner wall 18a of the Schlemm's canal 18. While the example opening 902 in FIG. 16 is depicted as a continuous, single lumen defining a fluid pathway, the opening may be defined an arrangement of adjacent pores forming a sponge like structure defining a fluid pathway or a combination thereof. While the example opening 902 in FIG. 16 is in the shape of a cube, the opening may have other geometric shapes.

The movement of the laser as it scans to affect the surgical volume 900 follows the treatment pattern P1, which is defined by a set of surgical parameters that include a treatment area A and a thickness t. The treatment area A is defined by a width w and a height h. The width may be defined in terms of a measure around the circumferential angle. For example, the width w may be defined in terms of an angle, e.g., 90 degrees, around the circumferential angle.

Referring to FIGS. 14 and 15, an initial placement of the laser focus within the eye is defined by a set of placement parameters, including a depth d and a location l. The location l defines a point around the circumferential angle of the eye at which laser treatment will begin, while the depth d defines a point between the anterior chamber 7 and the Schlemm's canal 18 where the laser treatment begins or ends. The depth d is measured relative to the region where the anterior chamber 7 meets the trabecular meshwork 12. Thus, a first point that is closer to the Schlemm's canal 18 side of the trabecular meshwork 12 may be described as being deeper than a second point that is closer to the anterior chamber 7 side of the trabecular meshwork 12. Alternatively, the second point may be described as being shallower than the first point.

With reference to FIG. 16, the opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18a of the Schlemm's canal 18, while the area A defines the cross-section size of the opening 902.

During a laser scanning procedure, a laser focus is moved to different depths d in ocular tissue and then scanned in two lateral dimensions or directions as defined by a treatment pattern P1 to affect a three-dimensional volume 900 of ocular tissue comprising multiple sheets or layers of affected tissue. The two lateral dimensions are generally orthogonal to the axis of movement of the laser focus. With reference to FIG. 16, the movement of a laser focus during laser scanning is described herein with reference to x, y, and z directions or axes, wherein: 1) movement of the laser focus to different depths d through the thickness t of treatment pattern P1 or the volume 900 of tissue corresponds to movement of the focus along the z axis, 2) movement of the laser focus in two dimensions or directions orthogonal to the z axis corresponds to movement of the laser focus along the width w of the treatment pattern P1 or the volume 900 of tissue in the x direction, and movement of the laser focus along the height h of the treatment pattern P1 or the volume 900 of tissue in the y direction.

As used herein scanning of the laser focus generally corresponds to a raster type movement of the laser focus in the x direction, the y direction, and the z direction. The laser focus may be located at a point in the z direction and then raster scanned in two dimensions or directions, in the x direction and the y direction. The focal point of the laser in the z direction may be referred to as a depth d within the treatment pattern P1 or the volume 900 of tissue. The two-direction raster scanning of the laser focus defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, on the order of a few micrometers (m), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Table 2 includes examples of treatment pattern parameters and surgical laser parameters for treating tissue. The range of the parameter set is limited by practical ranges for the repetition rate of the laser and the scanning speed of the scanners.

Other, non-rectangular and more irregular treatment patterns can also be programmed and created in the tissue. These irregular patterns can still be decomposed to spots, lines, and layers and their extent characterized by width, height, and depth. Examples of irregular treatment patterns

TABLE 2

| Tissue treated | Treatment pattern dimensions w[mm], h[mm], t[mm] | Opening cross section A [mm²] | Cell size w[μm], h[μm], t[μm] | Laser average power [W] | Laser repetition rate [kHz] | Laser pulse energy [μJ] | Procedure time [s] |
|---|---|---|---|---|---|---|---|
| Trabecular meshwork | 1.5, 0.2, 0.2 | 0.3 | 3, 3, 3 | 0.9 | 300 | 3 | 7.4 |
| Trabecular meshwork | 2, 0.2, 0.2 | 0.4 | 4, 4, 4 | 1 | 200 | 5 | 6.3 |
| Trabecular meshwork | 0.5, 0.2, 0.5 | 0.1 | 5, 5, 5 | 0.75 | 50 | 15 | 8.0 |
| Trabecular meshwork | 0.5, 0.2, 0.5 | 0.1 | 5, 5, 5 | 0.14 | 10 | 14 | 40.0 |
| Trabecular meshwork | 0.5, 0.2, 1.0 | 0.1 | 10, 10, 10 | 0.35 | 10 | 35 | 10.0 |
| Trabecular meshwork | 0.75, 0.25, 0.35 | 0.1875 | 10, 10, 10 | 0.7 | 20 | 35 | 3.3 |

Figures 17A, 17B:
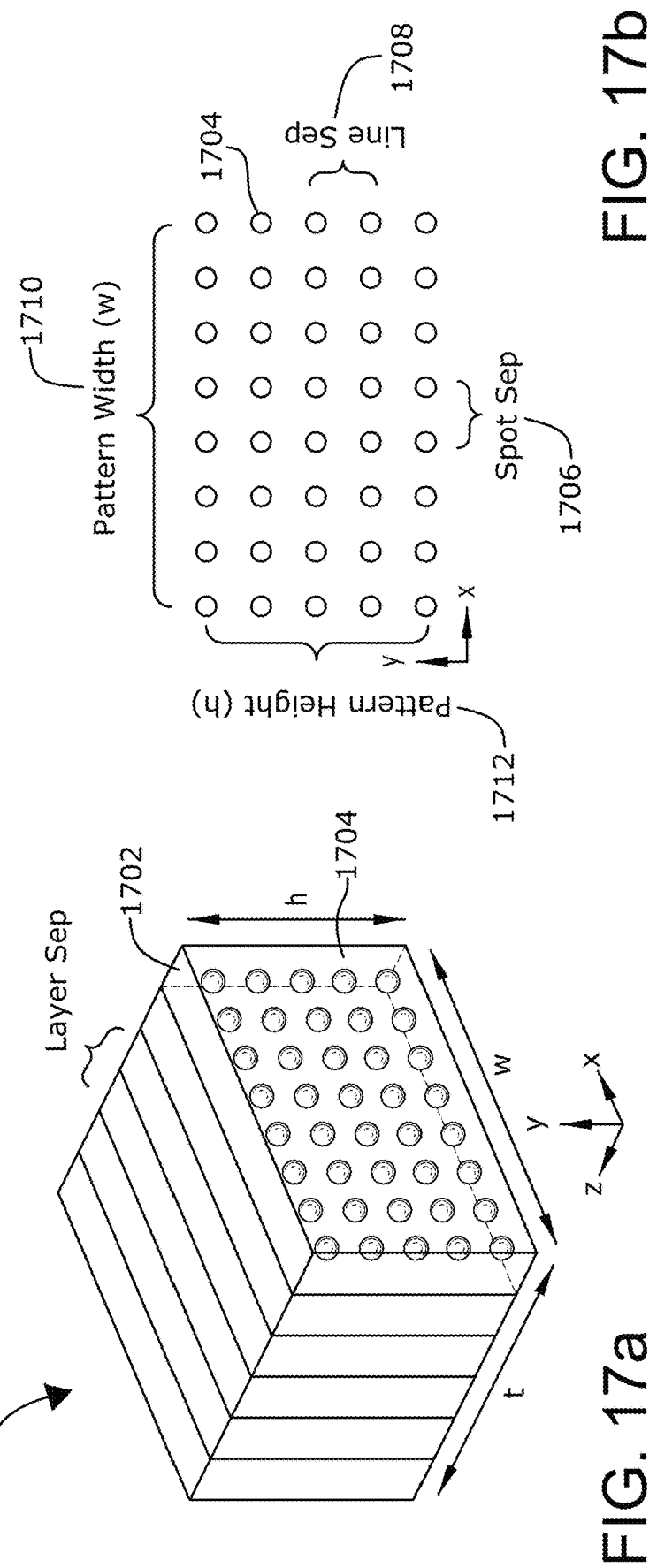
FIG. 17*a* is a schematic illustration of a three-dimensional laser treatment pattern formed by a number of stacked two-dimensional treatment planes or layers.
FIG. 17*b* is a schematic illustration of a two-dimensional treatment layer defined by an array of spots.

With reference to FIGS. 17a and 17b, a 3D treatment pattern P1 may be defined by a number of 2D treatment layers 1702 or treatment planes that are stacked to form a 3D treatment pattern characterized by a width w, height h, and depth or thickness t. Each individual treatment layer 1702 is in turn characterized by a pattern height h (equal to the height h of the 3D treatment pattern P1) and a pattern width w (equal to the width w of the 3D treatment pattern P1) and comprises an array of spots 1704 spaced apart to establish or fit within the height and width. The pattern width w corresponds to a distance along the circumference of the corneal angle parallel to the trabecular meshwork. This direction is also known as the circumferential direction. The pattern height h corresponds to a distance transverse to the circumference of the corneal angle perpendicular to the trabecular meshwork. This direction is also known as the azimuthal direction.

Each spot 1704 in the treatment pattern P1 corresponds to a site within a target volume of ocular tissue where optical energy is applied at a laser focus to create a micro-photo-disruption site. With reference to FIG. 17b, each spot 1704 in a treatment layer 1702 is separated from a neighboring spot by programmable distances called spot separation (Spot Sep 1706) and a line separation (Line Sep 1708). A treatment layer 1702 is completed with the programmed pattern width w 1710 and pattern height h 1712 is achieved. Each layer 1702 in the 3D treatment pattern P1 is separated from a neighboring layer by a layer separation (Layer Sep).

A treatment pattern P1 may be defined by a set of programmable parameters, such as shown in Table 3.

TABLE 3

| Parameter | Minimum | Maximum |
|---|---|---|
| width w | 10 μm | 2000 μm |
| height h | 10 μm | 2000 μm |
| depth/thickness t | 10 μm | 4000 μm |
| Spot Sep | 2 μm | 40 μm |
| Line Sep | 2 μm | 40 μm |
| Layer Sep | 2 μm | 200 μm |
| pulse energy | 0 μJ | 35 μJ | are described in U.S. Patent Application Publication No. 2021/0307964, entitled Method, System, and Apparatus for Generating Three-Dimensional Treatment Patterns for Laser Surgery of Glaucoma, the disclosure of which is hereby incorporated by reference.

In one example treatment pattern P1, the parameters are:
width=750 μm
height=250 μm
depth=350 μm
spot separation=10 μm
line separation=10 μm
layer separation=10 μm During laser treatment, each treatment layer 1702 is individually created by scanning the laser focus in two dimensions, e.g., width and height, or z and y, to the various spots 1704 defining the layer, while the focus is fixed at the third dimension, e.g., depth or Z. Once a treatment layer 1702 is created, the focus is moved in the depth or z direction and the next treatment layer in the stack is created. This process is repeated until all treatment layers 1702 in the 3D treatment pattern P1 are created.

Figure 18A:
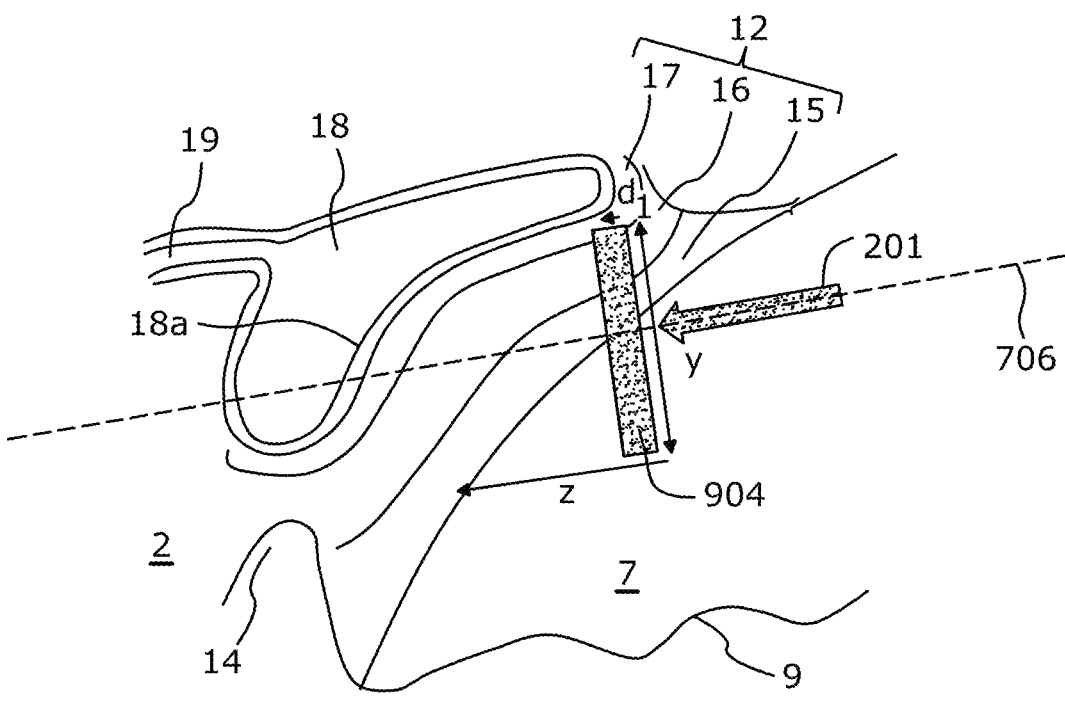
FIGS. 18*a* and 18*b* are schematic illustrations of two layers of a laser scanning process based on the treatment pattern of FIGS. 15, where the scanning begins at a shallow depth adjacent the anterior chamber and proceeds toward the Schlemm's canal.
Figure 18B:
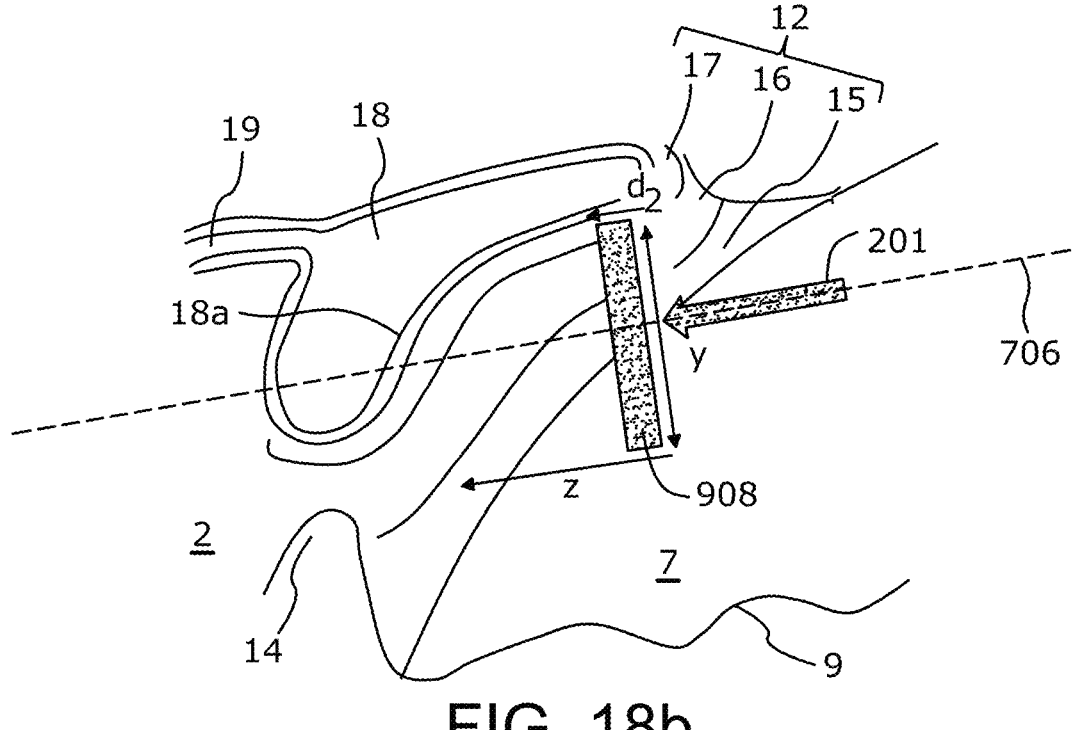

With reference to FIGS. 18a and 18b, in one type of laser treatment procedure the laser scanning of treatment layers begins at a shallow depth at the end of the treatment pattern P1 adjacent the anterior chamber 7 and proceeds, layer-by-layer, in a direction that generally corresponds to the direction of propagation of the laser beam 201. More specifically, and with reference to FIG. 18a, the laser scanning of treatment layers proceeds in the z direction toward an anatomical structure, e.g., the Schlemm's canal 18, while the direction of propagation of the laser beam 201 also proceeds toward same anatomical structure, e.g., the Schlemm's canal 18.

In FIG. 18a, the focus of the laser beam 201 is initially located at a depth $d_1$. The depth $d_1$ places the laser focus in an initial layer 904 of tissue. Once the laser focus is positioned at the initial depth $d_1$, the focus of the laser beam 201 is scanned in multiple directions while being maintained at the initial depth. With reference to FIG. 17a, the multiple directions are the x direction and y direction, where the x direction is into the plane of FIG. 18a. The focus of the visual observation apparatus 400 of the visualization system 826 remains fixed at the depth do while the laser beam 201 is being scanned.

With reference to FIG. 18b, the scanning of the focus of the laser beam 201 in the multiple directions results in the photodisruption of the initial layer 904 of tissue. The focus of the laser beam 201 is then moved along the laser axis 706 in the z direction toward the Schlemm's canal 18 to another depth $d_2$. This depth $d_2$ places the laser focus at a subsequent layer 908 of tissue deeper than the initial layer 904. Once the laser focus is positioned at the subsequent layer 908, the focus is scanned in multiple directions while being maintained at that depth.

Returning to FIG. 18b, after scanning of the subsequent layer 908, the focus of the laser beam 201 is moved in the z direction toward the Schlemm's canal 18 to additional depths and scanned through additional treatment layers 1702 until all layers of the target volume 60 of ocular tissue have been treated.

Figure 19A:
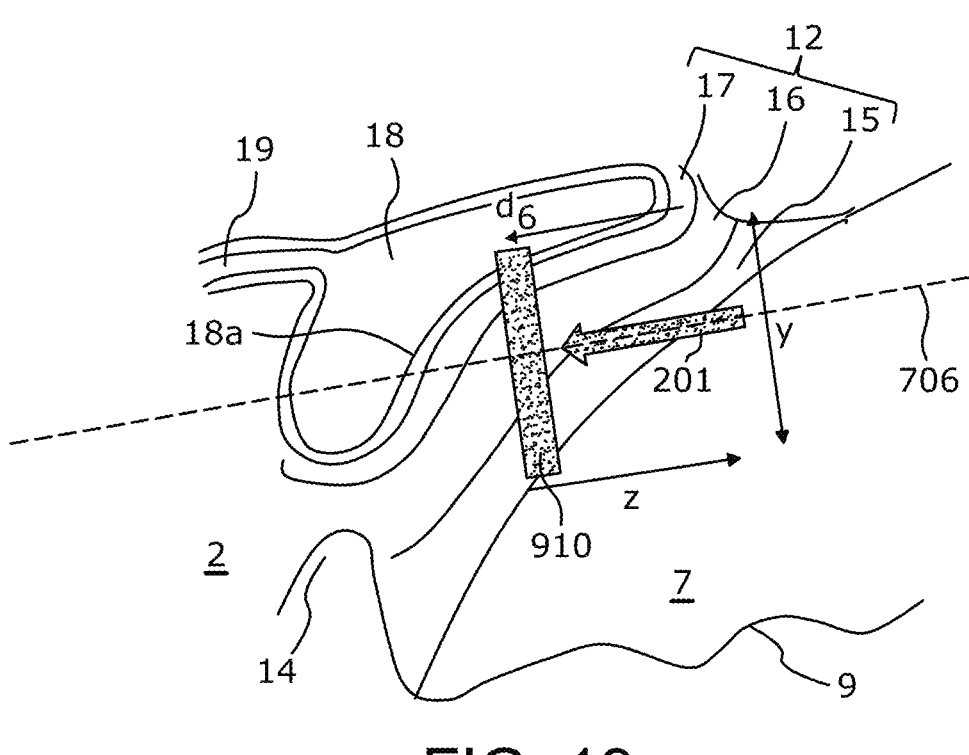
FIGS. 19*a* and 19*b* are schematic illustrations of two layers of a laser scanning process based on the treatment pattern of FIGS. 15, where the scanning begins at a deep depth adjacent the Schlemm's canal and proceeds toward the anterior chamber.
Figure 19B:
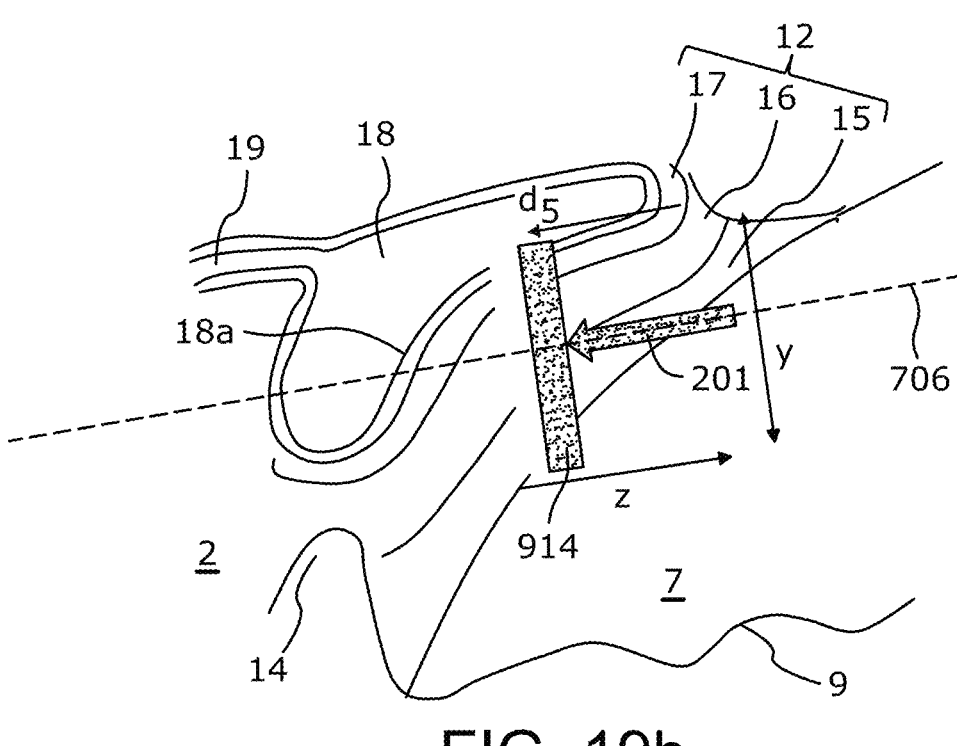

With reference to FIGS. 19a and 19b, in an alternative laser treatment procedure the laser scanning of treatment layers begins at a deep depth at the end of the treatment pattern P1 adjacent the Schlemm's canal 18 and proceeds, layer-by-layer, in a direction generally opposite to or against the direction of propagation of the laser beam 201. More specifically, and with reference to FIG. 19a, the laser scanning of treatment layers starts at an anatomical structure, e.g., the Schlemm's canal 18, and proceeds away from that structure in the z direction toward the anterior chamber 7, while the direction of propagation of the laser beam 201 proceeds toward the structure.

In FIG. 19a, the focus of the laser beam 701 is initially located at a depth $d_6$. The depth $d_6$ places the laser focus in an initial layer 910 of tissue. Once the laser focus is positioned at the initial depth $d_6$, the focus of the laser beam 201 is scanned in multiple directions while being maintained at the initial depth $d_6$. With reference to FIG. 17a, the multiple directions are the x direction and y direction, where the x direction is into the plane of FIG. 19a.

With reference to FIG. 19b, the scanning of the focus of the laser beam 201 in multiple directions results in the photodisruption of the initial layer 910 of tissue. The focus of the laser beam 201 is then moved along the laser axis 706 in the z direction toward the anterior chamber 7 to a subsequent depth $d_5$. The subsequent depth $d_5$ places the laser focus at a subsequent layer 914 of tissue less deep than the initial layer 910 of tissue. Once the laser focus is positioned at the subsequent depth $d_5$, the focus is scanned in multiple directions while being maintained at the subsequent depth $d_5$.

Returning to FIG. 19b, after scanning of the subsequent layer 914, the focus of the laser beam 201 is moved in the z direction toward the anterior chamber 7 to additional depths and scanned through additional layers until all treatment layers 1702 of the target volume 60 of ocular tissue have been treated.

In another treatment, instead of creating a treatment pattern P1 one treatment layer 1702 at a time, the focus of the laser beam 201 is scanned in three dimensions. For example, while the laser focus is being moved transversely through a height and/or width, e.g., in the x and/or y direction, the laser focus is also oscillated back and forth axially through a depth, e.g., in the z direction. The treatment pattern P1 characterized by such scanning of the laser focus may be referred to as a "clearing pattern." Oscillation of the laser focus through the depth in the z direction occurs simultaneous with transverse movement of the laser focus in the x and y directions. An example of scanning a laser in accordance with a clearing pattern is disclosed in U.S. patent application Ser. No. 17/202,257, the entire disclosure of which is hereby incorporated by reference.

Figure 20:
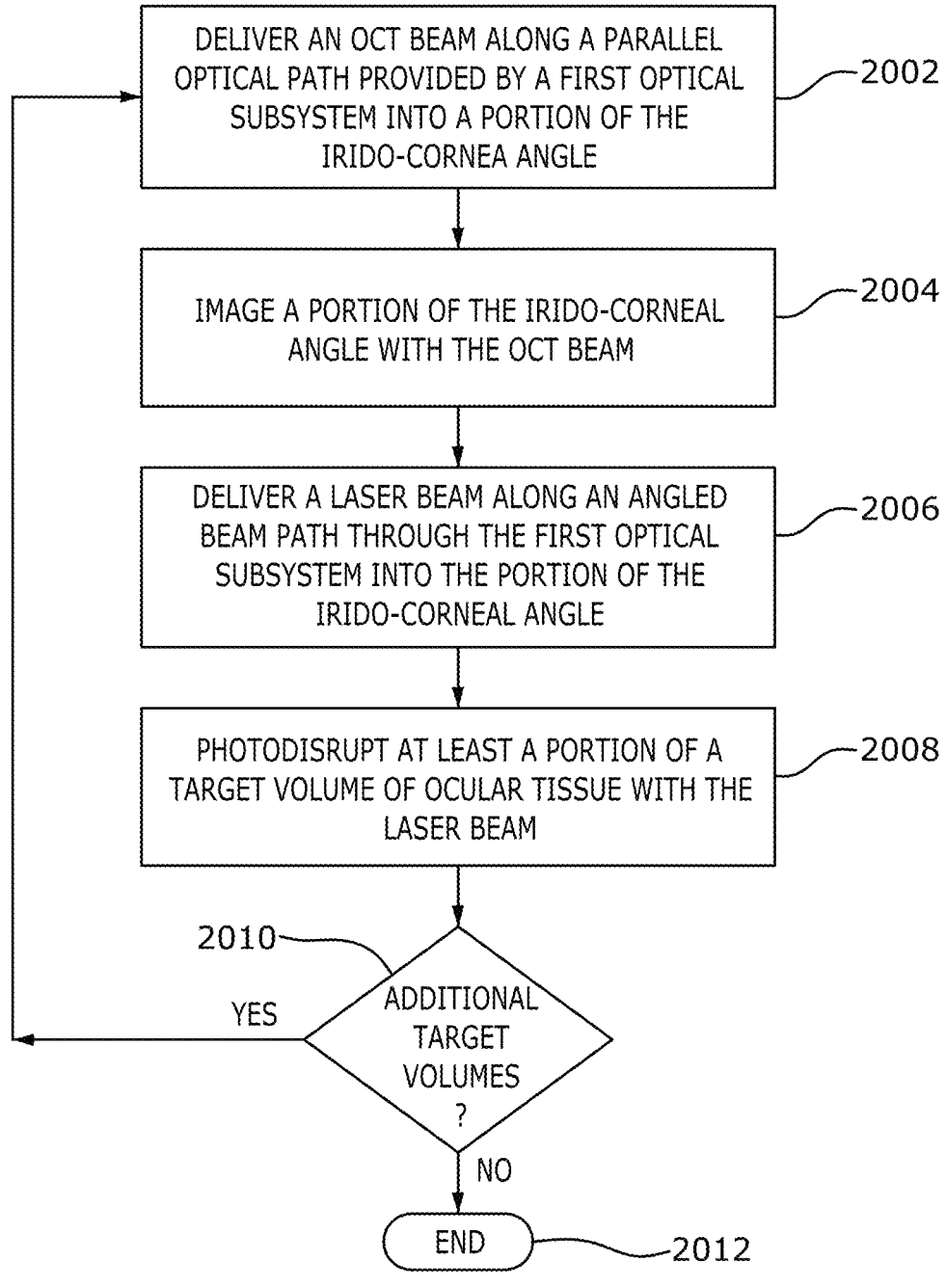
FIG. 20 is a flowchart of a method of imaging an eye and treating the eye through non-collinear laser and imaging paths.

With reference to FIG. 20, a method of imaging and treating an eye 1 having an optical axis 24, a cornea 3, an anterior chamber 7, and an irido-corneal angle 13 is disclosed. The method may involve the imaging of and laser treatment of one or more surgical volumes or target volumes of ocular tissue around the circumferential angle 13 of the eye 1 and may be performed by the integrated surgical system 1000 of FIGS. 8-9b having a first optical subsystem 1001 like one of those shown in FIG. 9c-10d. With reference to FIGS. 13a and 13b, the first optical subsystem 1001 is configured to couple to the eye 1 and includes a first optical subsystem axis 705 that substantially aligns with the optical axis 24 of the eye 1 when the first optical subsystem is coupled to the eye. Substantially aligned with means the first optical subsystem axis 705 is within 0-5 degrees of alignment with the optical axis 24 of the eye 1.

At block 2002 and with additional reference to FIGS. 8 and 13b, an OCT beam 301 of an OCT imaging apparatus 300 is delivered along an OCT optical path 707 (also referred to herein as an "OCT axis") that enters a first optical subsystem 1001 along an OCT input axis 707i, and exits the first optical subsystem along an OCT output axis 707o. The OCT output axis 707o is substantially parallel to the optical axis 24 of the eye 1, is radially offset from the optical axis, and extends through the cornea 3 and into a portion of the irido-corneal angle 13 at a point along a circumferential angle of the eye. A surgical volume 720, also referred to herein as a target volume of ocular tissue, is included in the portion of the irido-corneal angle 13. The OCT output axis 707o is radially offset from the optical axis 24 of the eye 1 by a distance such that the OCT beam 301 avoids the anterior chamber 7 of the eye. The distance may vary due to the size of the eye 1 and due to other anatomical parameters of the eye, such as cornea thickness and anterior and posterior radius of curvature. The OCT focusing lens 751 (e.g., with −75 mm focal length) included in the focusing objective head 700 is mounted to a linear stage. The linear stage movement adjusts the focus position of the OCT beam 301 to account for distance variation. Knowing patient biometry, this distance can be calculated.

With reference to FIG. 13b, the OCT beam 301 is delivered along the OCT optical path 707 by receiving the OCT beam along the OCT input axis 707i incident to an entry face 753 of the first optical subsystem 1001, and directing the OCT beam along an optical path through the first optical subsystem 1001 to the OCT output axis 707o. In some embodiments the entry face 753 is substantially flat and is a surface of a prism 752 of the first optical subsystem 1001. In some embodiments of the first optical subsystems 1001, such as shown in FIGS. 9c, 10a, 10b, and 13b, the OCT beam 301 is directed to the OCT output axis 707o by providing a linear OCT optical path 707 along the OCT input axis 707i through the first optical subsystem to the OCT output axis 707o. In other embodiments of the first optical subsystems 1001, such as shown in FIGS. 10c and 10d, the OCT beam 301 is directed to the OCT output axis 707o by reflecting the OCT beam off at least one reflective facet 757c, 757d, 759d of the first optical subsystem 1001.

In some embodiments, the OCT beam 301 is delivered along the OCT optical path 707 into the portion of the irido-corneal angle 13 with the surgical volume 720 by aligning the OCT output axis 707o of the OCT optical path with the portion of the irido-corneal angle. For example, with reference to FIGS. 11a and 12a, one or more optics of the first optical subsystem 1001 may be rotated about the subsystem axis 705 to align the OCT output axis 707o of the OCT optical path 707 with the portion of the irido-corneal angle 13. To this end, the one or more optics of the first optical subsystem 1001 may include a window 801 coupled to the cornea 3, an exit lens 710 having a surface 711 coupled to the window and a prism 752 coupled to the exit lens, and the exit lens and prism are rotated about the subsystem axis 705 without rotating the window. In other words, the window 801 remains fixed in place relative to the cornea 3 while the exit lens 710 and prism 752 rotate relative to the window.

Figure 21:
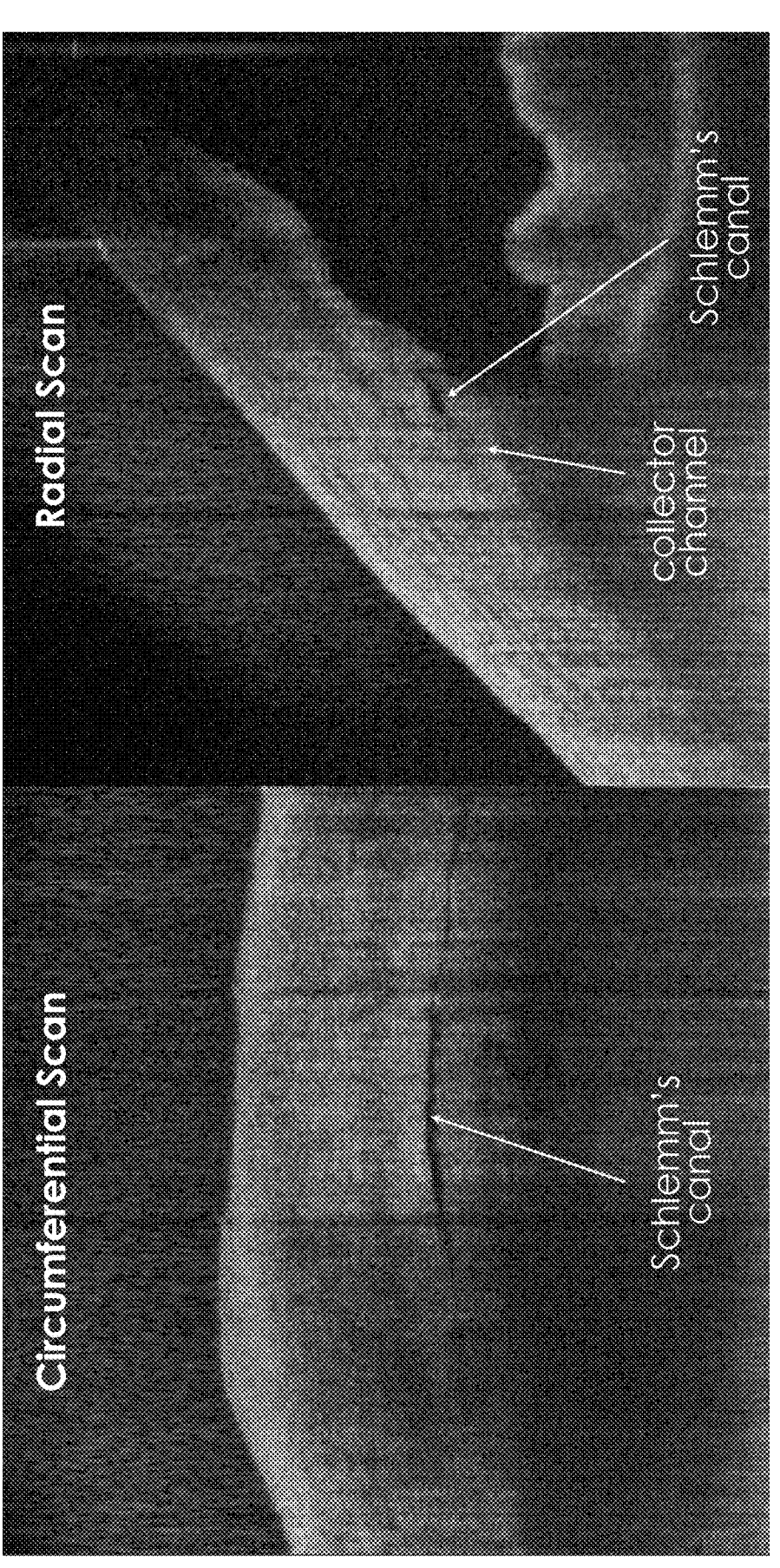
FIG. 21 are OCT images including an image resulting from a circumferential (or tangential) OCT scan and an image resulting from a radial OCT scan.

At block 2004, a portion of the irido-corneal angle 13 is imaged with the OCT beam 301. To this end, and with additional reference to FIG. 21, the OCT imaging apparatus 300 of the integrated surgical system 1000 is configured to obtain one or both of a tangential (or circumferential) scan of the portion of the irido-corneal angle 13 and a radial scan of the portion. The circumferential scan reveals various anatomy of the eye including the Schlemm's canal. The radial scan reveals various anatomy of the eye including the Schlemm's canal and collector channel.

At block 2006, a laser beam 201 is delivered along an angled optical path or laser axis 706 that extends through the first optical subsystem 1001, through the cornea 3, through the anterior chamber 7, and into the portion of the irido-corneal angle 13 that includes the target volume 720 of ocular tissue. With reference to FIG. 13a, the angled optical path 706 and the subsystem axis 705 are angularly offset from each other to intersect in the anterior chamber 7 of the eye 1, while the OCT optical path 707 and the angled optical path 706 are angularly offset from each other to intersect or meet in the irido-corneal angle 13 of the eye 1. With reference to FIG. 13b, the laser beam 201 is delivered along the angled optical path 706 into the portion of the irido-corneal angle 13 by receiving the laser beam along a laser input axis 706i incident to an entry surface 712 of the first optical subsystem 1001 and directing the laser beam through the optics, e.g., the exit lens 710 and the window 801, of the first optical subsystem and through the cornea 3 to the laser output axis 706o. In some embodiments the entry surface 712 is curved and is a surface of an exit lens 710 of the first optical subsystem 1001.

In some embodiments, the laser beam 201 is delivered along the laser optical path 706 into the portion of the irido-corneal angle 13 with the surgical volume 720 by aligning the laser output axis 706o of the laser optical path with the portion of the irido-corneal angle. For example, with reference to FIGS. 11a and 12a, one or more optics of the first optical subsystem 1001 may be rotated about the subsystem axis 705 to align the laser output axis 706o of the laser optical path 706 with the portion of the irido-corneal angle 13. To this end, the one or more optics of the first optical subsystem 1001 may include a window 801 coupled to the cornea 3, an exit lens 710 having a surface 711 coupled to the window, and a prism 752 coupled to the exit lens, and the exit lens and prism are rotated about the subsystem axis 705 without rotating the window. In other words, the window 801 remains fixed in place relative to the cornea 3 while the exit lens 710 and prism 752 rotate relative to the window.

At block 2008, at least a portion of the target volume 720 of ocular tissue is photodisrupted with the laser beam 201.

At block 2010, if no additional target volumes 720 of ocular tissue are to be treated, the process proceeds to block 2012 and ends. If another target volume 720 of ocular tissue is to be imaged and treated, the process returns to block 2002 and the delivering of the OCT beam, the imaging of block 2004, the delivering of the laser beam of block 2006, and the photodisrupting of block 2008 is repeated for another portion of the irido-corneal angle along the circumferential angle of the eye that includes the other target volume of ocular tissue. To this end, optics of the first optical subsystem 1001 may be rotated to align the parallel OCT optical path 707 and the angled laser optical path 706 with the other portion of the irido-corneal angle 13 that includes the other target volume 720 of ocular tissue.

While the method of FIG. 20 discloses imaging and photodisrupting in a sequence where imaging precedes photodisruption, the method is not limited in this manner. In some embodiments, the delivering of an OCT beam 301 to and imaging of a portion of the irido-corneal angle 13 with the OCT beam occurs prior to delivering a laser beam and photodisrupting the target volume of ocular tissue with the laser beam 201. In other embodiments, the delivering of an OCT beam 301 to and imaging of a portion of the irido-corneal angle 13 with the OCT beam occurs together with or simultaneously with while photodisrupting the portion of the target volume of ocular tissue with delivering a laser beam and photodisrupting the target volume of ocular tissue with the laser beam 201.

The various aspects of this disclosure are provided to enable one of ordinary skill in the art to practice the present invention. Various modifications to exemplary embodiments presented throughout this disclosure will be readily apparent to those skilled in the art. Thus, the claims are not intended to be limited to the various aspects of this disclosure but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An integrated surgical system for imaging and treating an eye having an optical axis, a cornea, an anterior chamber, and an irido-corneal angle, the integrated surgical system comprising:
   a laser source configured to output a laser beam;
   an OCT imaging apparatus configured to output an OCT beam;
   a first optical subsystem configured to:
      couple to the eye,
      receive the OCT beam along an OCT input axis incident to an entry face of the first optical subsystem, and to direct the OCT beam along an OCT optical path through the first optical subsystem to an OCT output axis that: 1) is within 20 degrees of parallel to the optical axis of the eye, 2) is radially offset from the optical axis of the eye, and 3) extends through the cornea and into a portion of the irido-corneal angle at a point along a circumferential angle of the eye while avoiding the anterior chamber, and receive the laser beam along a laser input axis incident to an entry surface of the first optical subsystem, and to direct the laser beam along an angled optical path through the first optical subsystem, through the cornea, through the anterior chamber, and into a target volume of ocular tissue in the portion of the irido-corneal angle, wherein the angled optical path is different from the OCT optical path;

a second optical subsystem optically coupled to the laser source, the OCT imaging apparatus, and the first optical subsystem and configured to:

deliver the laser beam to the first optical subsystem along the laser input axis, and deliver the OCT beam to the first optical subsystem along the OCT input axis; and a control system coupled to the laser source, the OCT imaging apparatus, and the second optical subsystem and configured to:

control the OCT imaging apparatus to output the OCT beam to the second optical subsystem, and to image the portion of the irido-corneal angle with the OCT beam, and control the laser source to output the laser beam to the second optical subsystem to photodisrupt at least a portion of the target volume of ocular tissue.

2. The integrated surgical system of claim 1, wherein the first optical subsystem comprises an entry face and the first optical subsystem is:

arranged to receive the OCT beam along the OCT input axis incident to the entry face, and configured to direct the OCT beam to the OCT output axis.

3. The integrated surgical system of claim 2, wherein the first optical subsystem is configured to provide a linear optical path along the OCT input axis to the OCT output axis.

4. The integrated surgical system of claim 2, wherein the first optical subsystem comprises at least one reflective facet and is configured to reflect the OCT beam off the at least one reflective facet to the OCT output axis.

5. The integrated surgical system of claim 1, wherein the first optical subsystem comprises a subsystem axis and is configured so that when coupled to the eye, the subsystem axis is substantially aligned with the optical axis of the eye and the OCT output axis is radially offset from the subsystem axis.

6. The integrated surgical system of claim 1, wherein the first optical subsystem comprises a subsystem axis, an entry face, and an entry surface spaced apart from the entry face, and the first optical subsystem is:

arranged to receive the OCT beam incident the entry face; and receive the laser beam incident the entry surface.

7. The integrated surgical system of claim 6, wherein the entry face is substantially flat, and the entry surface is convex curved.

8. The integrated surgical system of claim 1, wherein the first optical subsystem comprises a subsystem axis and one or more optics configured to rotate about the subsystem axis.

9. The integrated surgical system of claim 8, wherein the one or more optics comprises a window and an exit lens having a surface coupled to the window, and the exit lens is configured to rotate about the subsystem axis without rotating the window.

10. The integrated surgical system of claim 1, wherein the first optical subsystem comprises a subsystem axis, and the angled optical path and the subsystem axis are angularly offset from each other.

11. The integrated surgical system of claim 1, wherein the OCT output axis and the angled optical path are angularly offset from each other.

12. The integrated surgical system of claim 1, wherein:

the first optical subsystem comprises a subsystem axis and an entry surface, and the first optical subsystem is:

arranged to receive the laser beam along a laser input axis incident the entry surface and angularly offset from the subsystem axis.

13. The integrated surgical system of claim 1, further comprising a visualization observation subsystem configured to output an illumination beam and to receive a visual observation beam, wherein the first optical subsystem is arranged and configured to direct each of the illumination beam and the visual observation beam along one of the OCT optical path and the angled optical path.

* * * * *